US008961590B2

(12) United States Patent
Baillargeon et al.

(10) Patent No.: US 8,961,590 B2
(45) Date of Patent: Feb. 24, 2015

(54) FLEXIBLE HELICAL STENT HAVING DIFFERENT HELICAL REGIONS

(75) Inventors: Brian P. Baillargeon, Oakley, CA (US); Ramesh Marrey, Pleasanton, CA (US)

(73) Assignee: Cordis Corporation

( * ) Notice: Subject to any disclaimer, the term of this patent is extended or adjusted under 35 U.S.C. 154(b) by 154 days.

(21) Appl. No.: 13/196,475

(22) Filed: Aug. 2, 2011

(65) Prior Publication Data

US 2012/0029622 A1    Feb. 2, 2012

Related U.S. Application Data

(60) Provisional application No. 61/369,969, filed on Aug. 2, 2010.

(51) Int. Cl.
*A61F 2/06* (2013.01)
*A61F 2/915* (2013.01)
*A61F 2/88* (2006.01)

(52) U.S. Cl.
CPC ............ *A61F 2/915* (2013.01); *A61F 2/885* (2013.01); *A61F 2002/91508* (2013.01); *A61F 2002/91516* (2013.01); *A61F 2002/91575* (2013.01); *A61F 2002/91583* (2013.01); *A61F 2250/0014* (2013.01); *A61F 2250/0068* (2013.01); *A61F 2230/0054* (2013.01)
USPC ........................................................ 623/1.42

(58) Field of Classification Search
USPC .............................. 623/1.22, 1.15, 1.39–1.46
See application file for complete search history.

(56) References Cited

U.S. PATENT DOCUMENTS

| 4,733,665 | A | 3/1988 | Palmaz |
| 4,739,762 | A | 4/1988 | Palmaz |
| 4,776,337 | A | 10/1988 | Palmaz |
| 4,969,458 | A | 11/1990 | Wiktor |
| 5,061,275 | A | 10/1991 | Wallsten et al. |
| 5,102,417 | A | 4/1992 | Palmaz |

(Continued)

FOREIGN PATENT DOCUMENTS

| DE | 60122525 T2 | 12/2006 |
| EP | 1155664 A2 | 11/2001 |

(Continued)

OTHER PUBLICATIONS

International Searching Authority, Notification of Transmittal of the International Search Report and the Written Opinion of the International Searching Authority, Oct. 4, 2011.

*Primary Examiner* — Alvin Stewart

(57) ABSTRACT

The present invention relates to tubular stents that are implanted within a body lumen. The stent has a cylindrical shape defining a longitudinal axis and includes a proximal helical section, a distal helical section and an intermediate ring section there between. Each of the proximal and distal helical sections has of a plurality of longitudinally oriented strut members and a plurality of circumferentially oriented hinge members connecting circumferentially adjacent strut members to form a band, the band being wrapped about the longitudinal axis in a substantially helical manner to form a plurality of helical windings, wherein the distal helical section is wound about the longitudinal axis in the opposite direction from the proximal helical section. The intermediate ring section includes a plurality of longitudinally oriented strut members and a plurality of circumferentially oriented hinge members connecting circumferentially adjacent strut members to form an endless ring.

29 Claims, 36 Drawing Sheets

(56) References Cited

U.S. PATENT DOCUMENTS

| | | | |
|---|---|---|---|
| 5,741,333 A | 4/1998 | Frid | |
| 5,800,456 A | 9/1998 | Maeda et al. | |
| 5,807,404 A * | 9/1998 | Richter | 623/1.16 |
| 5,810,872 A * | 9/1998 | Kanesaka et al. | 623/1.15 |
| 5,911,754 A | 6/1999 | Kanesaka et al. | |
| 5,913,897 A | 6/1999 | Corso, Jr. et al. | |
| 5,922,021 A | 7/1999 | Jang | |
| 5,938,697 A | 8/1999 | Killion et al. | |
| 6,013,854 A | 1/2000 | Moriuchi | |
| 6,033,433 A | 3/2000 | Ehr et al. | |
| 6,042,597 A | 3/2000 | Kveen et al. | |
| 6,059,822 A | 5/2000 | Kanesaka et al. | |
| 6,066,169 A * | 5/2000 | McGuinness | 623/1.16 |
| 6,096,072 A | 8/2000 | Kanesaka et al. | |
| 6,106,548 A | 8/2000 | Roubin et al. | |
| 6,162,244 A * | 12/2000 | Braun et al. | 623/1.12 |
| 6,287,336 B1 * | 9/2001 | Globerman et al. | 623/1.3 |
| 6,352,552 B1 | 3/2002 | Levinson et al. | |
| 6,423,091 B1 | 7/2002 | Hojeibane | |
| 6,475,236 B1 | 11/2002 | Roubin et al. | |
| 6,488,703 B1 | 12/2002 | Kveen et al. | |
| 6,488,706 B1 | 12/2002 | Solymar | |
| 6,503,270 B1 * | 1/2003 | Richter et al. | 623/1.15 |
| 6,517,570 B1 * | 2/2003 | Lau et al. | 623/1.13 |
| 6,551,351 B2 * | 4/2003 | Smith et al. | 623/1.16 |
| 6,569,193 B1 | 5/2003 | Cox et al. | |
| 6,610,086 B1 * | 8/2003 | Kock et al. | 623/1.22 |
| 6,652,576 B1 | 11/2003 | Stalker | |
| 6,656,162 B2 | 12/2003 | Santini, Jr. et al. | |
| 6,730,116 B1 * | 5/2004 | Wolinsky et al. | 623/1.16 |
| 6,736,844 B1 * | 5/2004 | Glatt et al. | 623/1.22 |
| 6,746,479 B2 | 6/2004 | Ehr et al. | |
| 6,764,506 B2 | 7/2004 | Roubin et al. | |
| 6,764,507 B2 * | 7/2004 | Shanley et al. | 623/1.16 |
| 6,770,088 B1 * | 8/2004 | Jang | 623/1.16 |
| 6,783,543 B2 | 8/2004 | Jang | |
| 6,796,999 B2 * | 9/2004 | Pinchasik | 623/1.16 |
| 6,821,292 B2 * | 11/2004 | Pazienza et al. | 623/1.15 |
| 6,878,162 B2 * | 4/2005 | Bales et al. | 623/1.15 |
| 6,916,336 B2 * | 7/2005 | Patel et al. | 623/1.16 |
| 6,949,120 B2 | 9/2005 | Kveen et al. | |
| 7,041,130 B2 | 5/2006 | Santini, Jr. et al. | |
| 7,070,590 B1 | 7/2006 | Santini, Jr. et al. | |
| 7,131,993 B2 * | 11/2006 | Gregorich | 623/1.16 |
| 7,160,321 B2 * | 1/2007 | Shanley | 623/1.42 |
| 7,163,555 B2 | 1/2007 | Dinh | |
| 7,169,175 B2 * | 1/2007 | Cottone et al. | 623/1.22 |
| 7,169,179 B2 * | 1/2007 | Shanley et al. | 623/1.43 |
| 7,179,289 B2 * | 2/2007 | Shanley | 623/1.42 |
| 7,264,633 B2 * | 9/2007 | Bonsignore | 623/1.15 |
| 7,279,664 B2 * | 10/2007 | Weber | 219/635 |
| 7,326,241 B2 * | 2/2008 | Jang | 623/1.15 |
| 7,329,276 B2 * | 2/2008 | Smith et al. | 623/1.16 |
| 7,329,277 B2 * | 2/2008 | Addonizio et al. | 623/1.22 |
| 7,381,217 B2 * | 6/2008 | Tischler | 623/1.16 |
| 7,442,203 B2 | 10/2008 | Ehr et al. | |
| 7,540,881 B2 * | 6/2009 | Meyer et al. | 623/1.35 |
| 7,556,644 B2 * | 7/2009 | Burpee et al. | 623/1.22 |
| 7,637,939 B2 * | 12/2009 | Tischler | 623/1.22 |
| 7,666,223 B2 * | 2/2010 | Santos et al. | 623/1.42 |
| 7,682,384 B2 * | 3/2010 | Addonizio et al. | 623/1.22 |
| 7,686,843 B2 * | 3/2010 | Moore | 623/1.16 |
| 7,722,661 B2 * | 5/2010 | Lenz et al. | 623/1.15 |
| 7,763,067 B2 * | 7/2010 | Bales et al. | 623/1.22 |
| 7,766,960 B2 * | 8/2010 | Alexander et al. | 623/1.22 |
| 7,780,721 B2 * | 8/2010 | Bales et al. | 623/1.22 |
| 7,812,290 B2 * | 10/2010 | Weber | 219/635 |
| 7,820,229 B2 * | 10/2010 | Santos et al. | 427/2.1 |
| 7,824,439 B2 * | 11/2010 | Toyokawa | 623/1.16 |
| 7,842,083 B2 * | 11/2010 | Shanley et al. | 623/1.42 |
| 7,846,198 B2 * | 12/2010 | Hogendijk | 623/1.22 |
| 7,850,728 B2 * | 12/2010 | Shanley | 623/1.42 |
| 7,862,607 B2 * | 1/2011 | McDermott et al. | 623/1.16 |
| 7,862,608 B2 * | 1/2011 | Hogendijk et al. | 623/1.22 |
| 7,909,865 B2 * | 3/2011 | Shanley | 623/1.42 |
| 7,913,371 B2 * | 3/2011 | Klocke et al. | 29/453 |
| 7,914,570 B2 * | 3/2011 | Brown | 623/1.22 |
| 7,963,990 B2 * | 6/2011 | Johnson | 623/1.39 |
| 7,988,723 B2 * | 8/2011 | Beach et al. | 623/1.22 |
| 8,038,707 B2 * | 10/2011 | Bales et al. | 623/1.22 |
| 8,119,184 B2 * | 2/2012 | Hossainy et al. | 427/2.24 |
| 8,128,679 B2 * | 3/2012 | Casey | 623/1.22 |
| 8,152,842 B2 * | 4/2012 | Schlun | 623/1.2 |
| 8,157,858 B2 * | 4/2012 | Goto | 623/1.16 |
| 8,192,483 B2 * | 6/2012 | Nakano | 623/1.16 |
| 8,202,313 B2 * | 6/2012 | Shanley et al. | 623/1.16 |
| 8,221,496 B2 * | 7/2012 | Zhao | 623/1.42 |
| 8,292,945 B2 * | 10/2012 | Welsh et al. | 623/1.15 |
| 8,328,865 B2 * | 12/2012 | Bales et al. | 623/1.22 |
| 8,333,799 B2 * | 12/2012 | Bales et al. | 623/1.22 |
| 2001/0007955 A1 | 7/2001 | Drasler et al. | |
| 2002/0038145 A1 | 3/2002 | Jang | |
| 2002/0045935 A1 * | 4/2002 | Jang | 623/1.16 |
| 2002/0058990 A1 | 5/2002 | Jang | |
| 2002/0095206 A1 * | 7/2002 | Addonizio et al. | 623/1.15 |
| 2002/0116044 A1 * | 8/2002 | Cottone et al. | 623/1.2 |
| 2003/0055490 A1 | 3/2003 | Roubin et al. | |
| 2003/0149469 A1 * | 8/2003 | Wolinsky et al. | 623/1.11 |
| 2003/0199970 A1 * | 10/2003 | Shanley | 623/1.16 |
| 2004/0044400 A1 * | 3/2004 | Cheng et al. | 623/1.16 |
| 2004/0054399 A1 * | 3/2004 | Roth | 623/1.16 |
| 2004/0088043 A1 * | 5/2004 | Klein | 623/1.16 |
| 2004/0088044 A1 * | 5/2004 | Brown et al. | 623/1.16 |
| 2004/0093071 A1 | 5/2004 | Jang | |
| 2004/0106985 A1 * | 6/2004 | Jang | 623/1.16 |
| 2004/0133271 A1 * | 7/2004 | Jang | 623/1.42 |
| 2004/0148012 A9 * | 7/2004 | Jang | 623/1.15 |
| 2004/0149294 A1 * | 8/2004 | Gianchandani et al. | 128/879 |
| 2004/0172123 A1 * | 9/2004 | Lootz et al. | 623/1.15 |
| 2004/0225347 A1 * | 11/2004 | Lang | 623/1.15 |
| 2004/0230296 A1 * | 11/2004 | Brown et al. | 623/1.16 |
| 2004/0249446 A1 * | 12/2004 | Patel et al. | 623/1.16 |
| 2004/0249449 A1 * | 12/2004 | Shanley et al. | 623/1.43 |
| 2004/0267350 A1 | 12/2004 | Roubin et al. | |
| 2005/0021130 A1 * | 1/2005 | Kveen et al. | 623/1.16 |
| 2005/0033410 A1 | 2/2005 | Hogendijk et al. | |
| 2005/0159807 A1 | 7/2005 | Bales et al. | |
| 2006/0030934 A1 * | 2/2006 | Hogendijk et al. | 623/1.22 |
| 2006/0265050 A1 * | 11/2006 | Morris et al. | 623/1.16 |
| 2006/0276880 A1 * | 12/2006 | Neuss et al. | 623/1.15 |
| 2007/0005126 A1 | 1/2007 | Tischler | |
| 2007/0129786 A1 | 6/2007 | Beach et al. | |
| 2008/0097582 A1 * | 4/2008 | Shanley et al. | 623/1.22 |
| 2008/0147159 A1 | 6/2008 | Cottone et al. | |
| 2008/0300674 A1 | 12/2008 | Jang | |
| 2009/0254173 A1 | 10/2009 | Jang | |
| 2009/0306766 A1 * | 12/2009 | McDermott et al. | 623/1.16 |
| 2010/0004725 A1 * | 1/2010 | Zipse et al. | 623/1.2 |
| 2010/0131046 A1 * | 5/2010 | Santos et al. | 623/1.16 |
| 2010/0145433 A1 * | 6/2010 | Anukhin et al. | 623/1.16 |
| 2010/0211161 A1 * | 8/2010 | Dreher | 623/1.16 |
| 2010/0217380 A1 * | 8/2010 | Donovan et al. | 623/1.16 |
| 2010/0222868 A1 * | 9/2010 | Lenz et al. | 623/1.16 |
| 2010/0234936 A1 * | 9/2010 | Schlun | 623/1.16 |
| 2010/0292777 A1 * | 11/2010 | Meyer et al. | 623/1.16 |
| 2010/0331961 A1 * | 12/2010 | Goetzen et al. | 623/1.16 |
| 2011/0153003 A1 * | 6/2011 | Shanley et al. | 623/1.16 |
| 2011/0184507 A1 * | 7/2011 | Fischer, Jr. et al. | 623/1.16 |
| 2011/0190873 A1 * | 8/2011 | Lenz et al. | 623/1.16 |
| 2012/0004719 A1 * | 1/2012 | Gregorich et al. | 623/1.16 |
| 2012/0016462 A1 * | 1/2012 | Gregorich et al. | 623/1.16 |
| 2012/0029620 A1 * | 2/2012 | Schroeder | 623/1.16 |
| 2012/0029621 A1 * | 2/2012 | Schroeder | 623/1.16 |
| 2012/0029622 A1 * | 2/2012 | Baillargeon et al. | 623/1.16 |
| 2012/0226346 A1 * | 9/2012 | Boismier et al. | 623/1.16 |
| 2012/0303112 A1 * | 11/2012 | Armstrong et al. | 623/1.16 |
| 2012/0323308 A1 * | 12/2012 | Zhou | 623/1.16 |
| 2013/0035753 A1 * | 2/2013 | Chen et al. | 623/1.16 |

FOREIGN PATENT DOCUMENTS

| | | |
|---|---|---|
| EP | 1296615 A2 | 4/2003 |
| EP | 1318768 A2 | 6/2003 |
| EP | 1155664 A3 | 7/2003 |

(56) References Cited

FOREIGN PATENT DOCUMENTS

| | | |
|---|---|---|
| EP | 1397091 A1 | 3/2004 |
| EP | 1296615 B1 | 8/2006 |
| EP | 1772114 A1 | 4/2007 |
| EP | 1155664 B1 | 11/2007 |
| EP | 1318768 B1 | 12/2008 |
| EP | 2111829 A1 | 10/2009 |
| JP | 2003534870 A | 11/2003 |
| JP | 2004508880 A | 3/2004 |
| JP | 2004528928 A | 9/2004 |
| WO | WO 0189421 A2 | 11/2001 |
| WO | WO 0193781 A2 | 12/2001 |
| WO | WO 0224109 A2 | 3/2002 |
| WO | WO 0189421 A3 | 4/2002 |
| WO | WO 0193781 A3 | 4/2002 |
| WO | WO 02024109 A3 | 12/2002 |
| WO | WO 02098326 A1 | 12/2002 |
| WO | WO 03015664 A1 | 2/2003 |
| WO | WO 03017870 A1 | 3/2003 |
| WO | WO 2004058100 A2 | 7/2004 |
| WO | WO 2008049045 A2 | 4/2008 |

\* cited by examiner

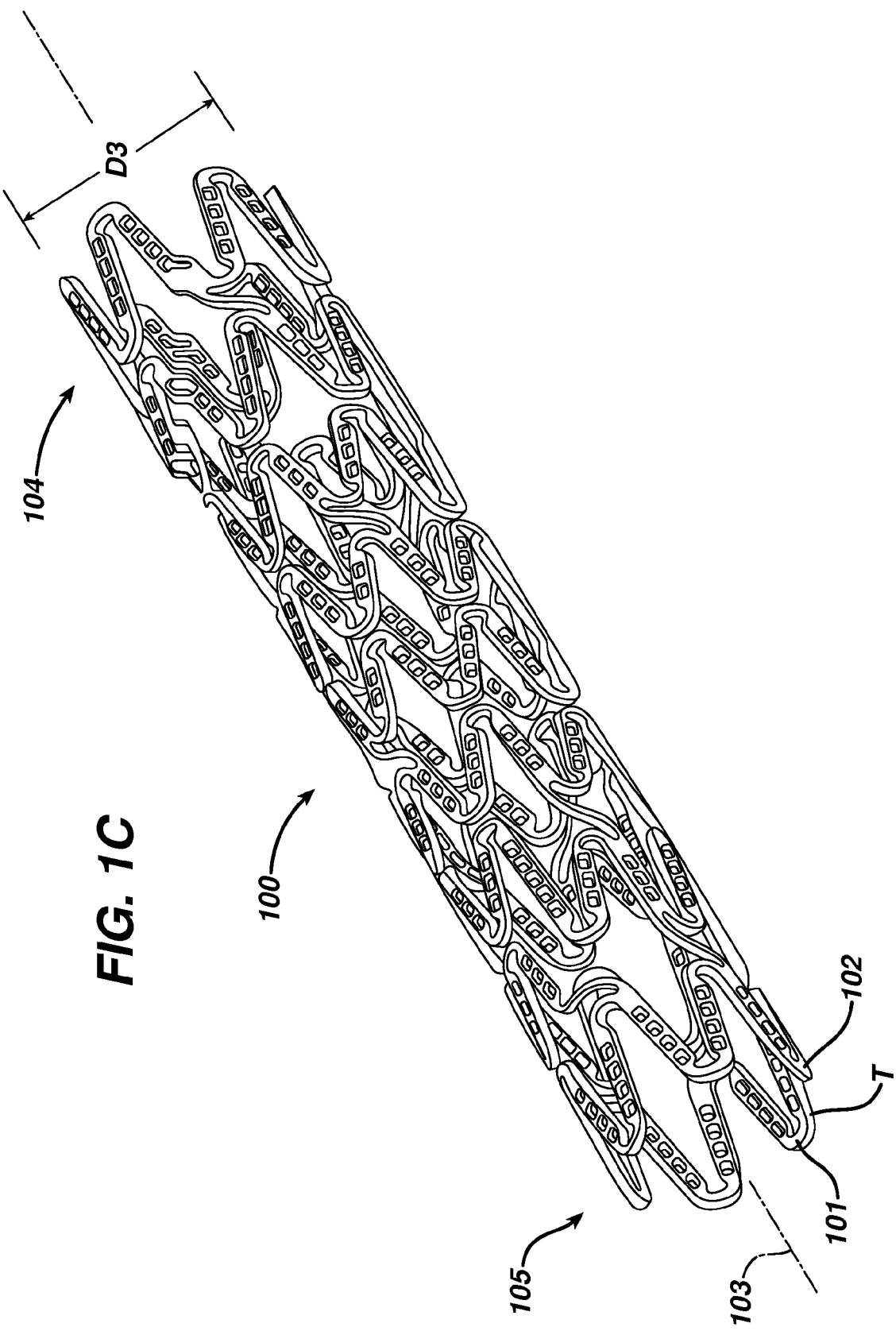

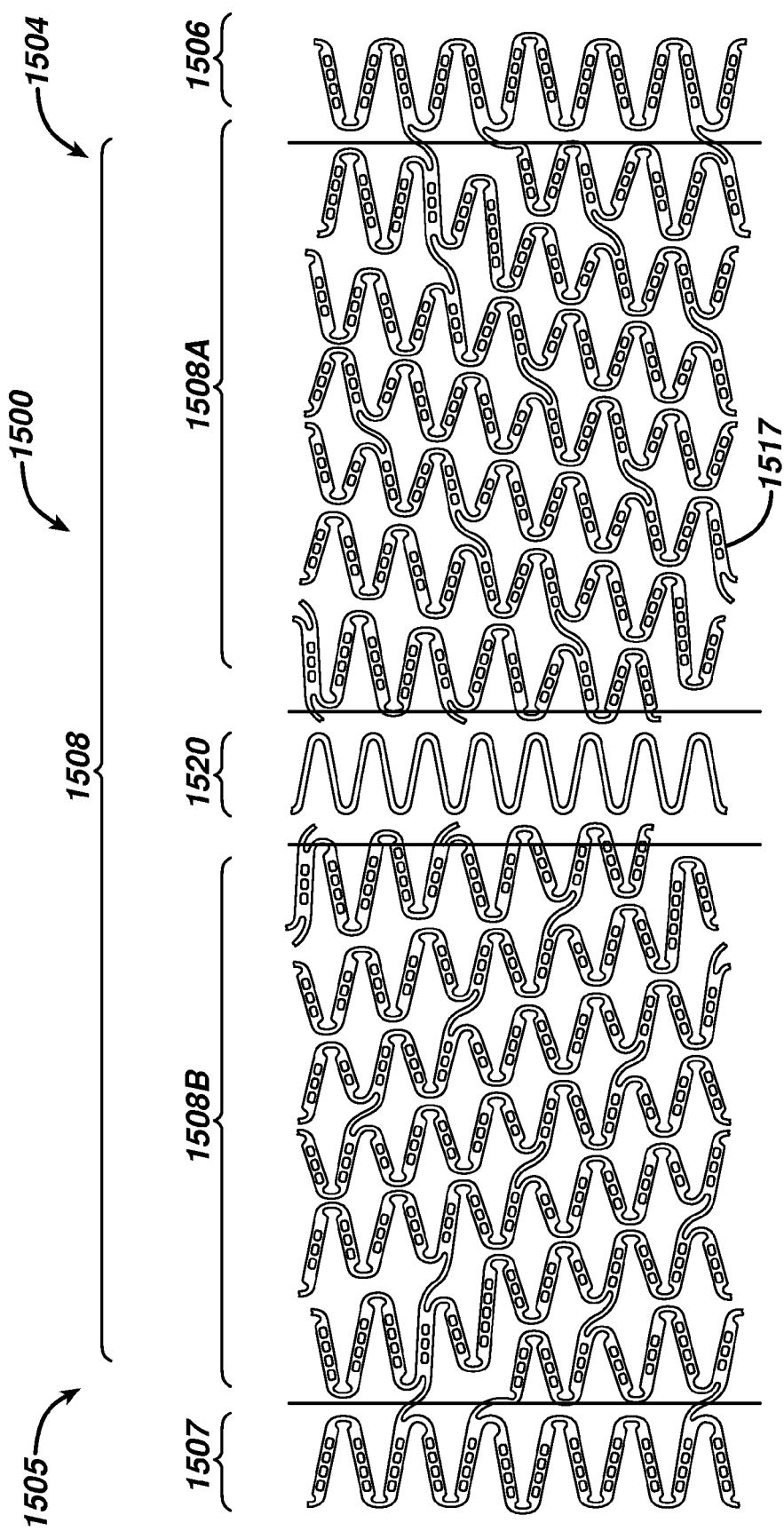

FLEXIBLE HELICAL STENT HAVING DIFFERENT HELICAL REGIONS

CROSS REFERENCE TO RELATED APPLICATION

This application claims the benefit of U.S. Provisional Application Ser. No. 61/369,969 filed Aug. 2, 2010, which is incorporated by reference herein.

BACKGROUND OF THE INVENTION

1. Field of the Invention

The present invention relates to tissue-supporting medical devices and drug delivery systems, and more particularly to expandable devices that are implanted within a body lumen of a living animal or human to support the organ, maintain patency and/or deliver drugs or agents.

2. Summary of the Related Art

In the past, permanent or biodegradable devices have been developed for implantation within a body passageway to maintain patency of the passageway and/or locally deliver drug or agent. These devices are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, typically referred to as stents, become encapsulated within the body tissue and remain a permanent implant.

Known stent designs include monofilament wire coil stents (U.S. Pat. No. 4,969,458); welded metal cages (U.S. Pat. Nos. 4,733,665 and 4,776,337); and, most prominently, thin-walled metal cylinders with axial slots formed around the circumference (U.S. Pat. Nos. 4,733,665, 4,739,762, and 4,776,337). Known construction materials for use in stents include polymers, organic fabrics and biocompatible metals, such as, stainless steel, gold, silver, tantalum, titanium, cobalt chromium and shape memory alloys such as Nitinol.

U.S. Pat. Nos. 4,733,665, 4,739,762, and 4,776,337 disclose expandable and deformable interluminal vascular grafts in the form of thin-walled tubular members with axial slots allowing the members to be expanded radially outwardly into contact with a body passageway. After insertion, the tubular members are mechanically expanded beyond their elastic limit and thus permanently fixed within the body. The force required to expand these tubular stents is proportional to the thickness of the wall material in a radial direction. To keep expansion forces within acceptable levels for use within the body (e.g., 5-10 atm), these designs must use very thin-walled materials (e.g., stainless steel tubing with 0.0025 inch thick walls). However, materials this thin are not visible on conventional fluoroscopic and x-ray equipment and it is therefore difficult to place the stents accurately or to find and retrieve stents that subsequently become dislodged and lost in the circulatory system.

Further, many of these thin-walled tubular stent designs employ networks of long, slender struts whose width in a circumferential direction is two or more times greater than their thickness in a radial direction. When expanded, these struts are frequently unstable, that is, they display a tendency to buckle, with individual struts twisting out of plane. Excessive protrusion of these twisted struts into the bloodstream has been observed to increase turbulence, and thus encourage thrombosis. Additional procedures have often been required to attempt to correct this problem of buckled struts. For example, after initial stent implantation is determined to have caused buckling of struts, a second, high-pressure balloon (e.g., 12 to 18 atm) would be used to attempt to drive the twisted struts further into the lumen wall. These secondary procedures can be dangerous to the patient due to the risk of collateral damage to the lumen wall.

In addition, many of the known stents display a large elastic recovery, known in the field as "recoil," after expansion inside a lumen. Large recoil necessitates over-expansion of the stent during implantation to achieve the desired final diameter. Over-expansion is potentially destructive to the lumen tissue. Known stents of the type described above experience recoil of up to about 6 to 12% from maximum expansion.

Large recoil also makes it very difficult to securely crimp most known stents onto delivery catheter balloons. As a result, slippage of stents on balloons during interlumenal transportation, final positioning, and implantation has been an ongoing problem. Many ancillary stent securing devices and techniques have been advanced to attempt to compensate for this basic design problem. Some of the stent securing devices include collars and sleeves used to secure the stent onto the balloon.

Another problem with known stent designs is non-uniformity in the geometry of the expanded stent. Non-uniform expansion can lead to non-uniform coverage of the lumen wall creating gaps in coverage and inadequate lumen support. Further, over expansion in some regions or cells of the stent can lead to excessive material strain and even failure of stent features. This problem is potentially worse in low expansion force stents having smaller feature widths and thicknesses in which manufacturing variations become proportionately more significant. In addition, a typical delivery catheter for use in expanding a stent includes a balloon folded into a compact shape for catheter insertion. The balloon is expanded by fluid pressure to unfold the balloon and deploy the stent. This process of unfolding the balloon causes uneven stresses to be applied to the stent during expansion of the balloon due to the folds causing the problem non-uniform stent expansion.

It is desirable to provide flexibility in stents to facilitate introduction of the stent into vessels that are difficult to reach. Often, however, characteristics of the stent that provide longitudinal flexibility, which is desirable when introducing the stent into the vessel, can be disadvantageous in terms of keeping the stent in an expanded condition. For example, stents formed from interconnected rings with closed cell structures or generally diamond-shaped cells are typically less flexible than stents formed from one or more helices, but are usually more uniformly and consistently expandable than helical stents. It is desirable to provide a stent with substantial flexibility that is adapted to be expanded in a uniform and consistent fashion.

In WO 03/015664, which is incorporated by reference, a stent having interconnected struts with openings for drug delivery is disclosed. However, elements for bridging the struts are generally thinner and spaced further apart than the struts. Thus, for such drug-eluting stents, the bridging element can provide an area of reduced or less consistent drug delivery. It is desirable to provide a drug-eluting stent in which areas of reduced or less consistent drug delivery can be reduced.

SUMMARY OF THE INVENTION

The present invention relates to tissue-supporting medical devices and drug delivery systems, and more particularly to expandable, devices that are implanted within a body lumen of a living animal or human to support the organ, maintain patency and/or deliver drugs or agents.

In one embodiment of the invention the flexible stent has proximal and distal end portions and a cylindrical shape, with luminal and abluminal surfaces and a thickness there between. The cylindrical shape defines a longitudinal axis. The stent further comprises a proximal helical section, a distal helical section and an intermediate ring section there between, each of the proximal and distal helical sections having of a plurality of longitudinally oriented strut members and a plurality of circumferentially oriented hinge members connecting circumferentially adjacent strut members to form a band, the band being wrapped about the longitudinal axis in a substantially helical manner to form a plurality of helical windings. The distal helical section is wound about the longitudinal axis in the opposite direction from the proximal helical section. The intermediate ring section includes a plurality of longitudinally oriented strut members and a plurality of circumferentially oriented hinge members connecting circumferentially adjacent strut members to form an endless ring. The intermediate ring section is attached to the distal end of the proximal helical section and the proximal end of the distal helical section by at least one connector members.

BRIEF DESCRIPTION OF THE DRAWINGS

FIG. 1C is a perspective view of a flexible stent in the "as cut" (manufactured) state according to one embodiment of the present invention.

FIG. 32 is a plan view of a flexible stent according to one embodiment of the present invention.

DETAILED DESCRIPTION OF THE INVENTION

The stent of the present invention is very flexible and deliverable, while still providing sufficient radial strength to maintain vessel patency. The stent can be formed in any suitable manner, such as by laser cutting a tube made from a suitable material, including cobalt chromium alloys, stainless steel alloys or nickel titanium alloys. Although coronary flexible stents of the present invention are disclosed to illustrate one embodiment of the present invention, one of ordinary skill in the art would understand that the disclosed invention can be equally applied to other locations and lumens in the body, such as, for example, vascular, non-vascular and peripheral vessels, ducts, and the like.

In accordance with one aspect of the present invention, the flexible stent is designed to be crimped down to a reduced diameter and percutaneously delivered through a body lumen to a target site by a delivery catheter. The target site may be, for example, a cardiac artery. Once deployed the flexible stent functions to maintain vessel patency and, if desired, deliver controlled amounts of drug or agent.

Figure 1A:
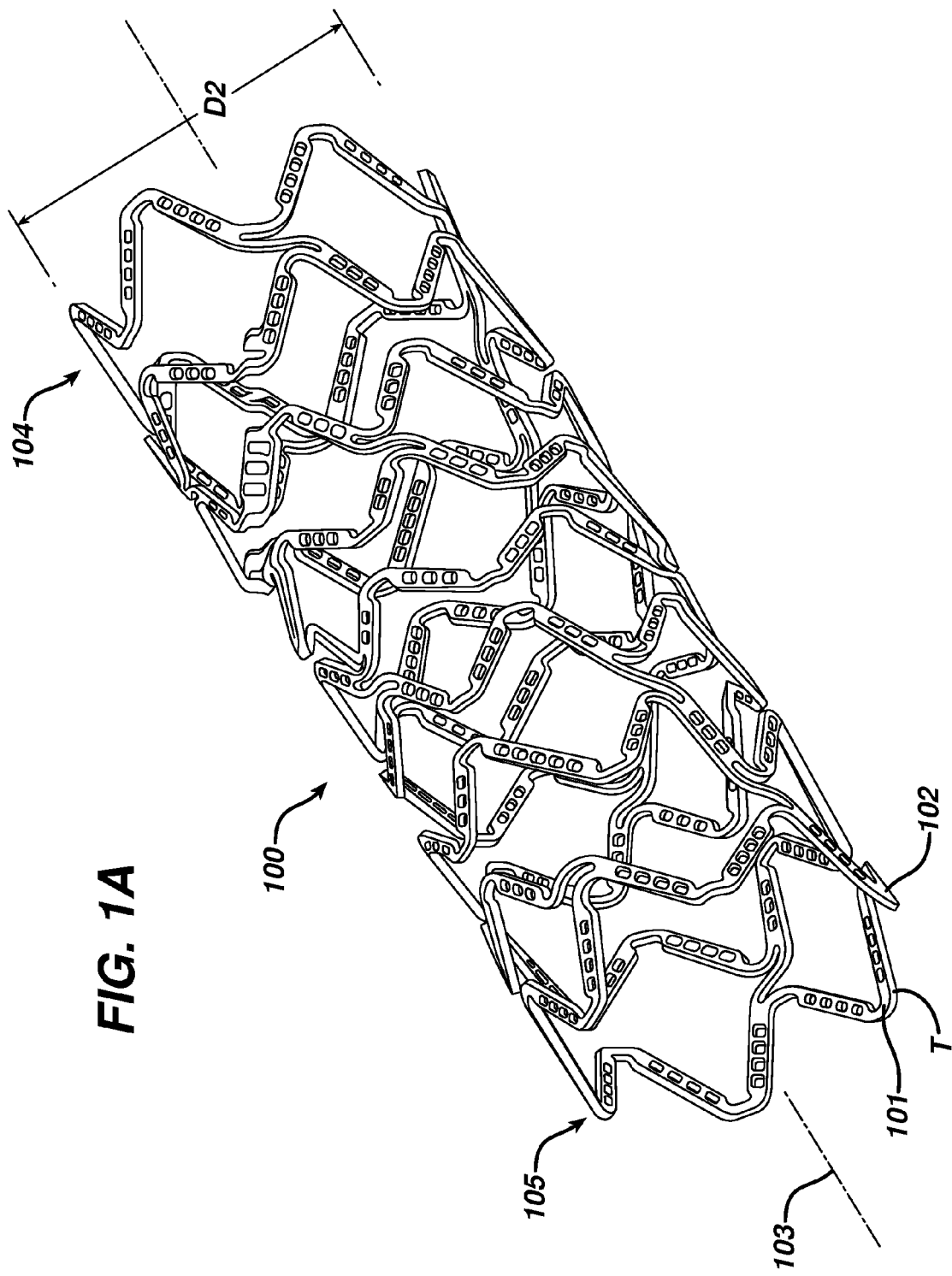
FIG. 1A is a perspective view of a flexible stent in the expanded (deployed) state according to one embodiment of the present invention.
Figure 1B:
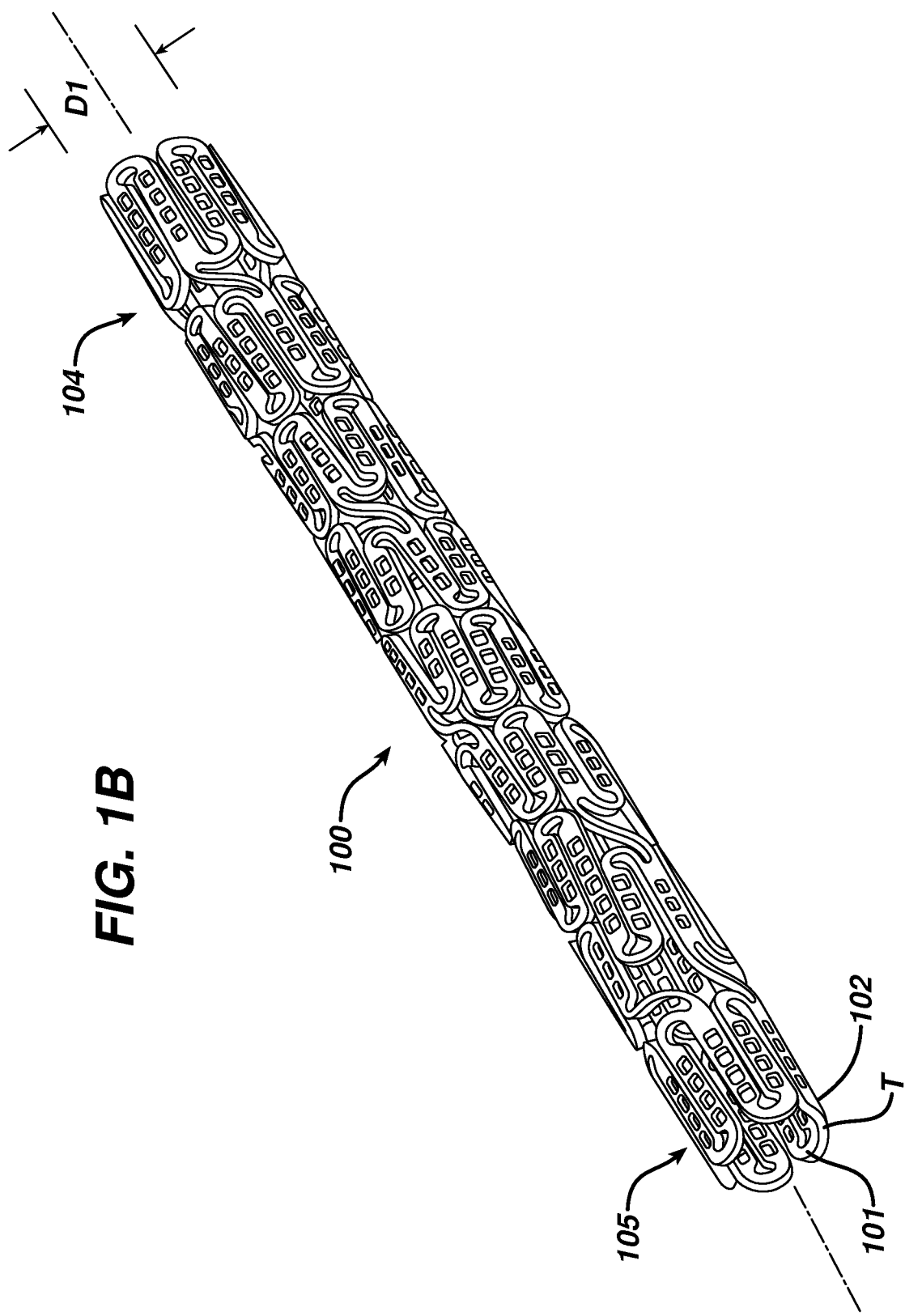
FIG. 1B is a perspective view of a flexible stent in the crimped state according to one embodiment of the present invention.

Perspective views of a flexible stent 100 in the expanded (deployed), crimped, and "as cut" or manufactured state according to one embodiment of the present invention are illustrated in FIGS. 1A, 1B and 1C respectively. The stent 100 has an "as cut" diameter when first manufactured of D3, as illustrated in FIG. 1C. The stent 100 is crimped down to a first diameter D1, illustrated in FIG. 1B, for insertion into a patient and navigation through the vessels, and a second diameter D2, illustrated in FIG. 1A, for deployment into the target area of a vessel, with the second diameter being greater than the first diameter.

The flexible stent 100 is cylindrical with a tubular configuration of structural elements having luminal and abluminal surfaces, 101, 102 respectively, and thickness (wall thickness) "T" there between. The cylindrical shape of the stent defines a longitudinal axis 103 and has proximal and distal ends portions 104, 105 respectively.

The terms proximal and distal are typically used to connote a direction or position relative to a human body. For example, the proximal end of a bone may be used to reference the end of the bone that is closer to the center of the body. Conversely, the term distal can be used to refer to the end of the bone farthest from the body. In the vasculature, proximal and distal are sometimes used to refer to the flow of blood to the heart, or away from the heart, respectively. Since the flexible stent described in this invention can be used in many different body lumens, including both the arterial and venous system, the use of the terms proximal and distal in this application are used to describe relative position in relation to the direction of delivery. For example, the use of the term distal end portion in the present application describes the end portion of the stent first introduced into the vasculature and farthest from the entry point into the body relative to the delivery path. Conversely, the use of the term proximal end portion is used to describe the back end portion of the stent that is closest to the entry point into the body relative to the delivery path.

Figure 2:
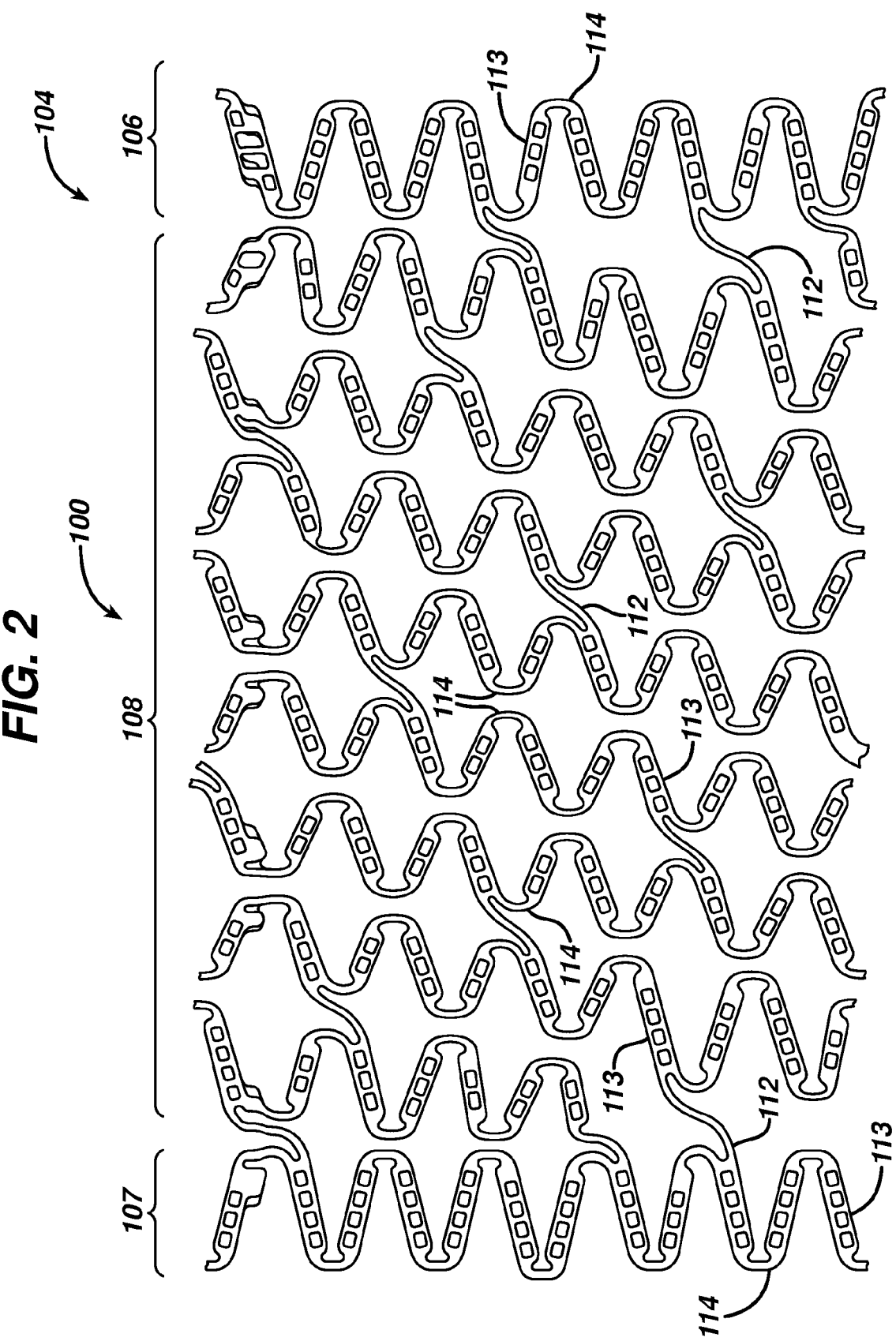
FIG. 2 is a plan view of a flexible stent according to one embodiment of the present invention.
Figure 3:
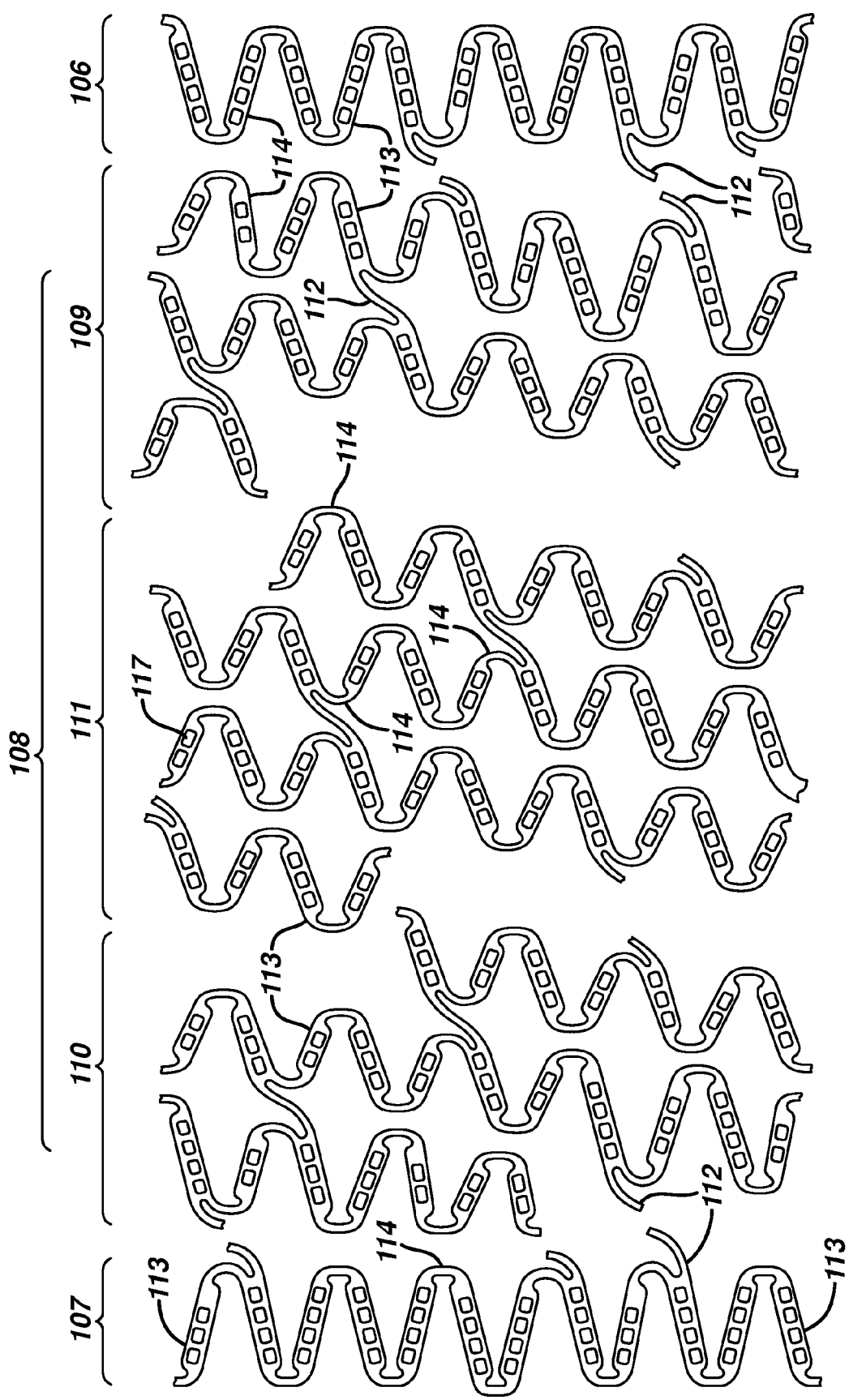
FIG. 3 is an exploded plan view of the flexible stent of FIG. 2.

FIGS. 2 and 3 are plan views of the stent 100 in a partially expanded condition according to one embodiment of the present invention. As used herein, the term plan view is understood to be a two-dimensional (2-D) view of a stent that has been cut along the longitudinal axis and laid out flat, such that the bottom edge could be wrapped around a cylinder and connected to the top edge.

The stent 100 architecture generally includes ring-like end sections 106, 107 along the proximal and distal ends, 104, 105 respectively, and a helical interior section 108 there between. The helical interior section 108 further includes a central zone 111 and proximal and distal transition zones 109, 110 respectively. The transition zones 109, 110 transition between the central zone 111 and the proximal and distal ring-like end sections 106, 107. FIG. 3 is an exploded plan view of the stent 100 illustrating the different sections and zones.

The stent 100 includes a plurality of longitudinally oriented struts 113 connected by a series of circumferentially oriented ductile hinges 114. Circumferentially adjacent struts 113 are connected at opposite ends by the hinges 114 in a substantially S or Z shaped sinusoidal-like pattern to form a band. Flexible connectors 112 are distributed throughout the stent 100 architecture for structural stability under a variety of loading conditions. The stent design illustrated in FIGS. 1 through 3 have a flexible connector geometry, however, a wide variety of connector geometries are contemplated. See generally FIGS. 6B through 6H.

The region in the stent 100 where the interior helical section 108 is first connected to the ring-like end sections 106, 107 is referred to as an anchor point, and the hinge 114 at that location is referred to as an "anchor hinge". This "take off" point may vary based on design constraints. Additionally, the incident angle, strut thickness, strut width, hinge width, hinge length, depot position and size, and connection length may vary based on optimization and design constraints.

As used herein the terms longitudinally, circumferentially and radially oriented are known to denote a particular direction relative to the stent 100 and the longitudinal axis 103. A longitudinally oriented member is directed, end to end (along its axis), generally in the direction of the longitudinal axis 103. It is obvious after reviewing the figures that the longitudinal direction of the strut 113 is closer to being parallel to the longitudinal axis when the stent 100 is in the crimped state as illustrated in FIG. 1B, then when the stent 100 is in the expanded, deployed state as illustrated in FIG. 1A. Regardless, in each case, the strut 113 is considered to be longitudinally oriented as the axis of the strut 113 is substantially oriented in the same direction as the longitudinal axis. A circumferentially oriented member, such as hinge 114, is directed substantially along the circumference of the tubular stent 100. Similarly, a radial direction or radially oriented is along a radius that extends generally from the longitudinal axis outward to the circumference of the tubular stent 100 in cross-section.

Figure 4A:
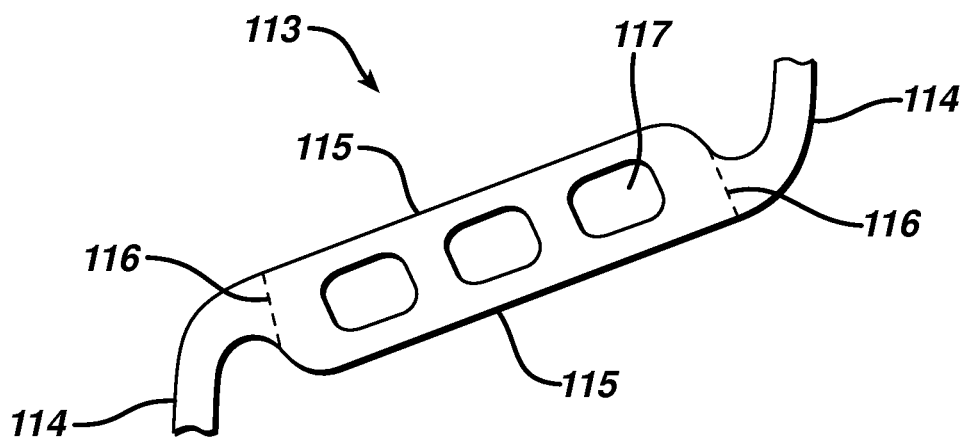
FIG. 4A is a close-up plan view of a strut from a flexible stent according to one embodiment of the present invention.
Figure 4B:
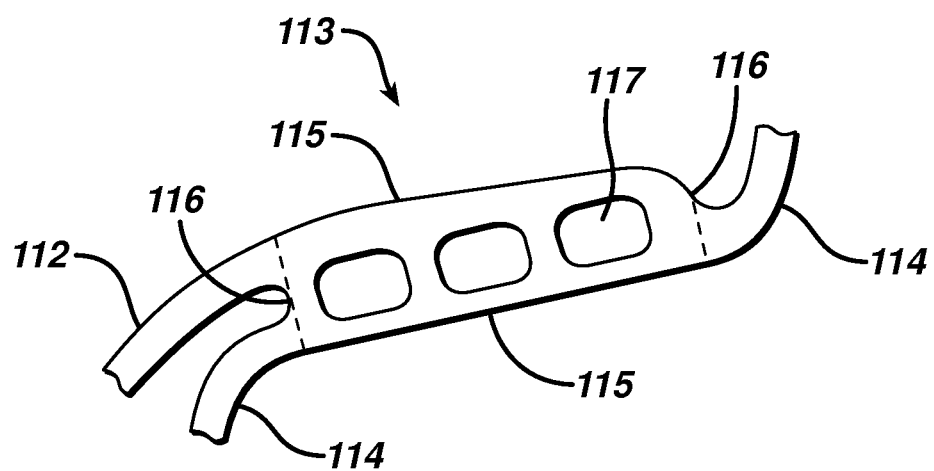
FIG. 4B is a close-up plan view of a strut from a flexible stent according to one embodiment of the present invention.
Figure 4C:
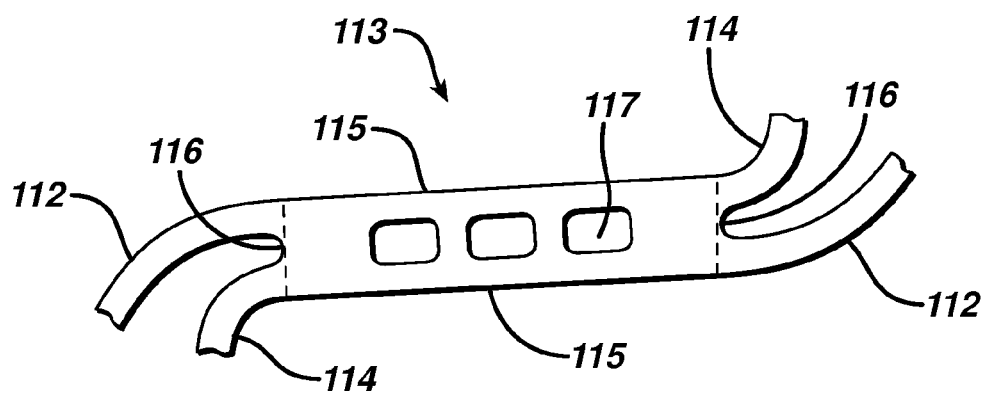
FIG. 4C is a close-up plan view of a strut from a flexible stent according to one embodiment of the present invention.

FIGS. 4A, 4B and 4C illustrate typical struts 113 according to various embodiments of the present invention. Each strut 113 is a substantially rectangular shaped member having longitudinally extending long sides 115 and circumferentially extending short sides 116. Opposing long sides 115 and short sides 116 may be substantially parallel to one another forming a near perfect rectangular as depicted by the strut 113 illustrated in FIG. 4A, or may be canted or angled to form a tapered strut 113 as depicted by the strut 113 illustrated in FIG. 4B. As can be seen in FIGS. 4A and 4B, the hinges 114 attached to the strut 113 along the short sides 116 of the strut, however the width of the strut (length of the short side 116) is greater than the width of the hinge 114 in a preferred embodiment of the invention. As illustrated in FIG. 4B, the flexible connectors 112 connect to the struts 113 along the short sides 116 of the struts 113, but do not connect to the hinges 114.

FIG. 4C represents a unique strut 113 that may be found in some embodiments of the stent 100 design. The strut 113 depicted in FIG. 4C is characterized by two connection points to circular hinges 114 (as hereinafter described) and two connection points to flexible connectors 112. This strut 113 is widest at the proximal and distal ends (at the connection points of the hinges 114 and flexible connectors 112) and tapers to its minimum width near the mid-point in the longitudinal strut 113 length. That is to say the length of the short side 116 of the strut 113 depicted in FIG. 4C is greater than the width near the longitudinal center point of the strut 113.

The struts 113 may have one or more depots 117 for containing at least one agent. The depots 117 may be any form of recess, channel, hole or cavity capable of holding an agent, but are preferably through holes precisiouly formed through the stent 100. In a preferred embodiment, the through hole passes through the strut from the luminal to abluminal surface. This preferred configuration may allow an agent or agents to be delivered both in a radially inward and outward direction along the luminal and abluminal sides of the stent 100. In addition, the depots 117 may be filled with a polymer inlay, either alone or containing one or more agents in solution or otherwise. Various depots 117 in the same stent may be filled with the same or different agents, and may have the same or different concentrations of agents. Any individual depot 117 may be filed with one or multiple agents, and the agents may be separated by a barrier layer. The barrier layer may be position in various configurations in the depot 117 as need to separate the agents. In a preferred embodiment, the barrier layer is oriented parallel to the luminal stent surface.

Figure 4D:
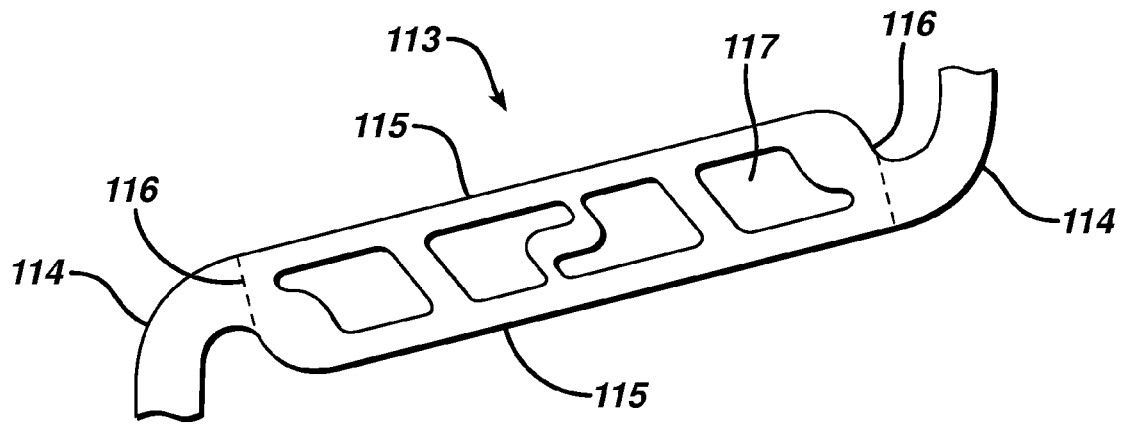
FIG. 4D is a close-up plan view of an organically optimized strut from a flexible stent according to one embodiment of the present invention.

The struts 113 may have symmetrically sized depots 117 as illustrated in FIGS. 4A-4C, or may include organically optimized depots 117 as illustrated in FIG. 4D. Organically optimized depots 117 are designed to maximize the depot 117 volume for any given strut 113 size, while reducing the stress state of the entire feature through the addition or removal of material critical to maintaining structural integrity upon stent 100 expansion.

As the term is used herein, the agent can be any therapeutic or pharmaceutic agent or drug, including the following: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which don't have the capacity to synthesize their own asparagine; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); Anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; Indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressive: (cyclosporine, tacrolimus (FK-506), sirolimus (rapamycin), azathioprine, mycophenolate mofetil); angiogenic: vascular endothelial growth factor (VEGF), fibroblast growth factor (FGF); nitric oxide donors; anti-sense oligo nucleotides and combinations thereof.

One or more agents may be distributed in one or more of the depots 117, along at least a portion of the luminal or abluminal stent 100 surfaces, or any combination of depots and/or stent surfaces. In a preferred embodiment, the agent is distributed in the depots 117 only, such that the exposed agent surface area is limited to the cross-sectional area of the depot opening in the stent 100 surface (luminal, abluminal or both). This design allows for agent delivery from the stent 100 having a surface area upon insertion into the patient that is substantially bare metal. In a preferred embodiment, the exposed bare metal surface area of the stent 100 is between 40 and 95 percent upon insertion of the stent 100 into a patient, and is most preferably approximately 75 percent bare metal upon insertion of the stent 100 into a patient. That is, the surface area of the stent 100 is approximately 25 percent agent and approximately 75 percent bare metal. As the agent is released, the stent 100 becomes a purely bare metal stent.

In a preferred embodiment, the depots 117 are distributed nearly uniformly throughout the strut pattern to provide a consistent agent dosage per unit surface area of the deployed stent 100 independent of the diameter or length of the stent used. The struts 113 may be of varying lengths, incident angle, depot configuration, and widths as needed to meet the product design.

Figure 5A:
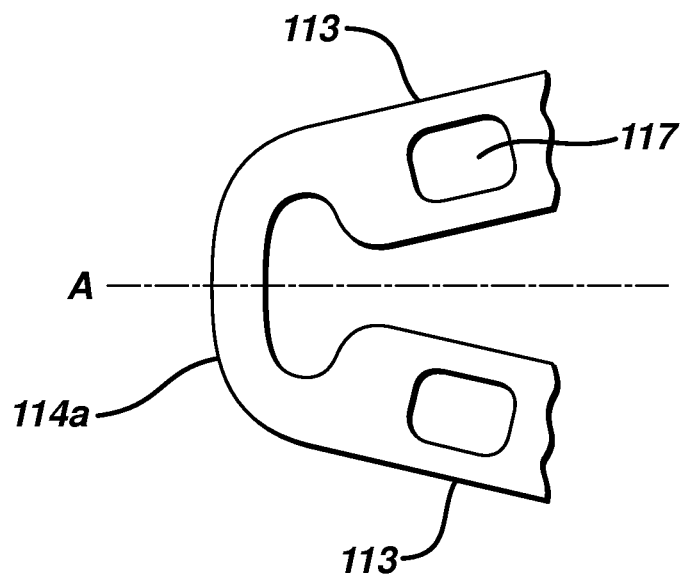
FIG. 5A is a close-up plan view of a ductile hinge from a flexible stent according to one embodiment of the present invention.
Figure 5B:
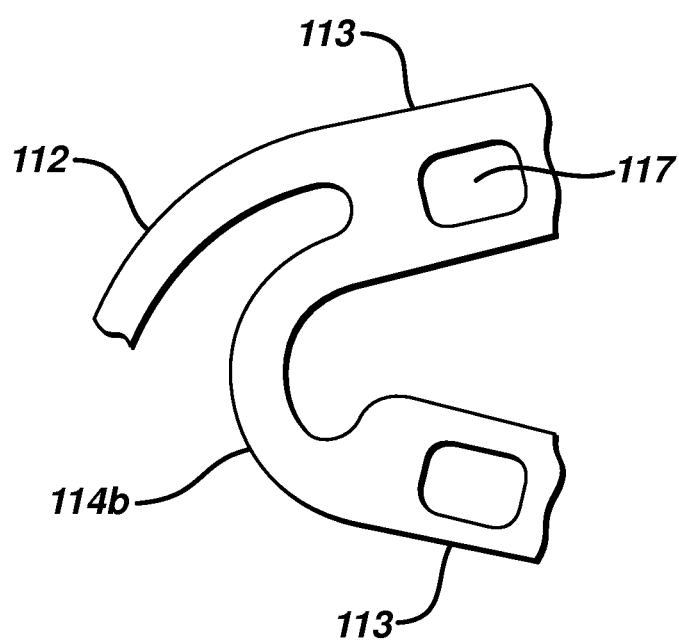
FIG. 5B is a close-up plan view of a ductile hinge from a flexible stent according to one embodiment of the present invention.

Ductile hinges 114 are used as the connection element between two circumferentially adjacent struts 113. There are two types of ductile hinges 114 found in stent 100. FIGS. 5A and 5B illustrate the two typical ductile hinges found in one embodiment of the present invention. FIG. 5A represents a single "free hinge" 114a that connects two circumferentially adjacent struts 113. In a preferred embodiment, this free hinge 114a is "C" shaped and is substantially symmetric about reference line "A" drawn though the apex point on the curved section. FIG. 5B represents a ductile hinge 114b that connects two circumferentially adjacent struts 113, where one of the struts is further connected to a flexible connector 112. This ductile hinge 114b is more circular in shape than the "C" shaped free hinge 114a disclosed in FIG. 5A, and is sometimes referred hereto as a "circular hinge" 14b. Although free hinges 114a and connector hinges 114b are identified separately here, they are sometimes generally both referred to as ductile hinges 114. The regions surrounding the circular hinge 14b is referred to as a circular hinge region. While the flexible connector 112 and circular ductile hinge 114b both connect to the same short side 116 of the strut 113 in the circular hinge region, they are not connected to one another.

Figure 6A:
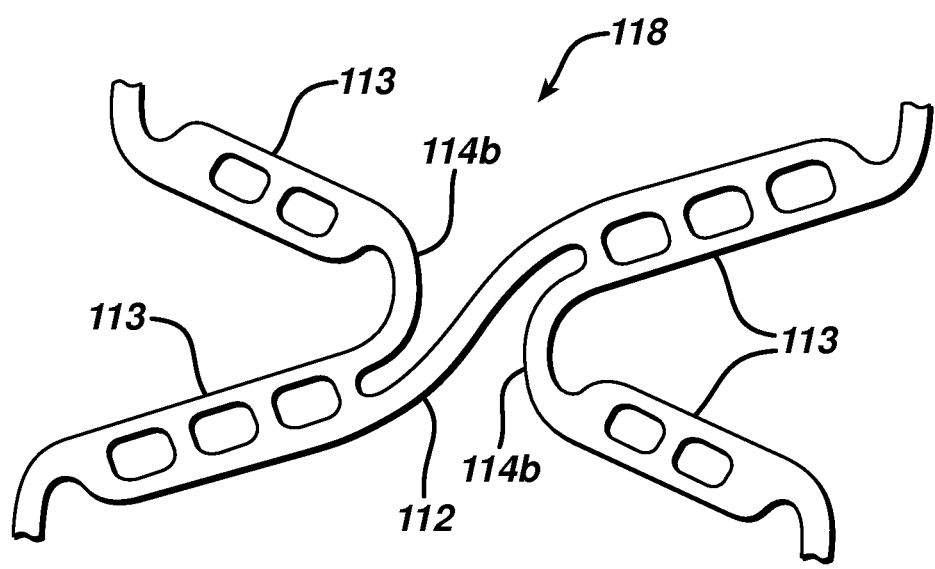
FIG. 6A is a close-up plan view of a circular hinge region from a flexible stent according to one embodiment of the present invention.
Figure 6B:
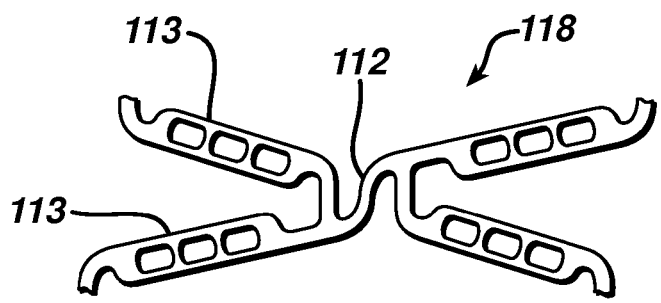
FIG. 6B is a close-up plan view of a circular hinge region from a flexible stent according to one embodiment of the present invention.
Figure 6C:
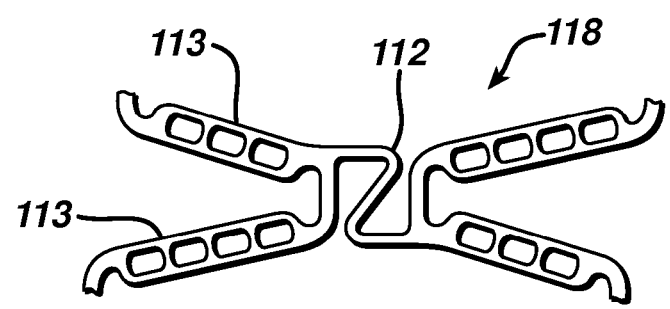
FIG. 6C is a close-up plan view of a circular hinge region from a flexible stent according to one embodiment of the present invention.
Figure 6D:
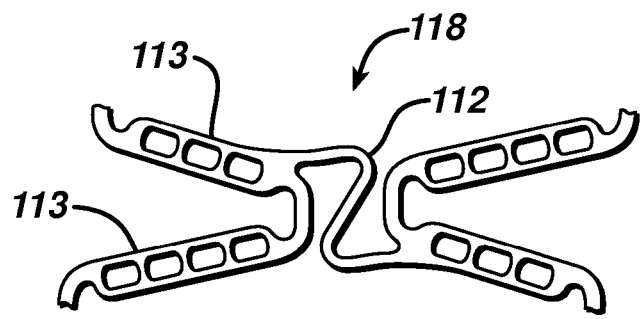
FIG. 6D is a close-up plan view of a circular hinge region from a flexible stent according to one embodiment of the present invention.
Figure 6E:
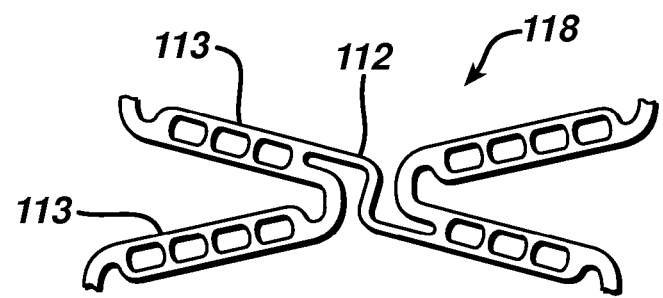
FIG. 6E is a close-up plan view of a circular hinge region from a flexible stent according to one embodiment of the present invention.
Figure 6F:
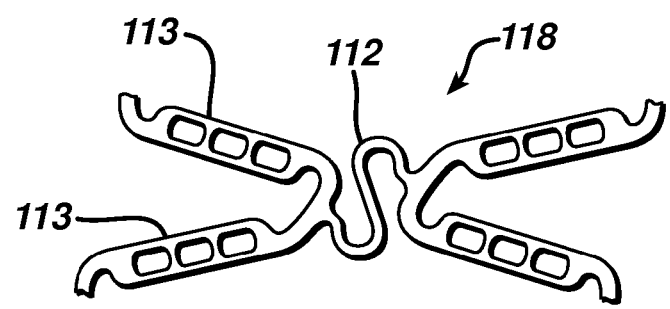
FIG. 6F is a close-up plan view of a circular hinge region from a flexible stent according to one embodiment of the present invention.
Figure 6G:
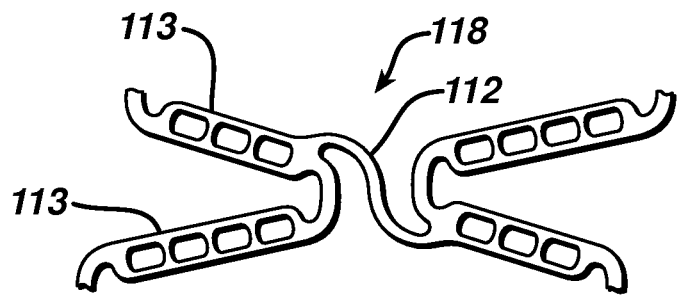
FIG. 6G is a close-up plan view of a circular hinge region from a flexible stent according to one embodiment of the present invention.
Figure 6H:
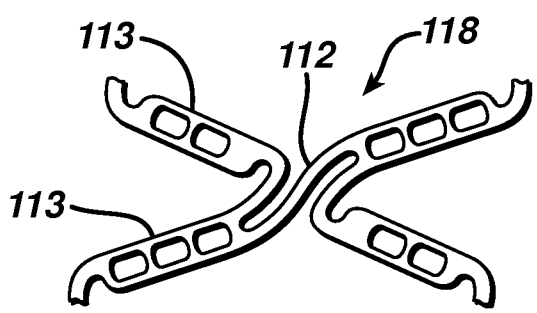
FIG. 6H is a close-up plan view of a circular hinge region from a flexible stent according to one embodiment of the present invention.
Figure 6I:
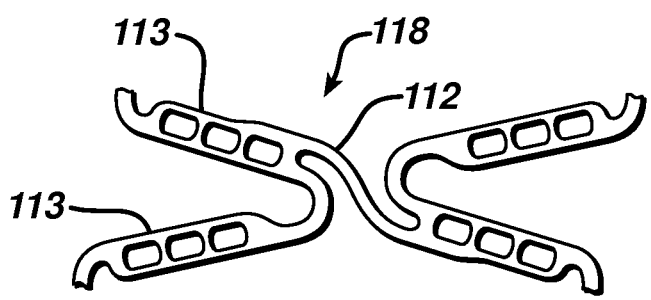
FIG. 6I is a close-up plan view of a circular hinge region from a flexible stent according to one embodiment of the present invention.
Figure 6J:
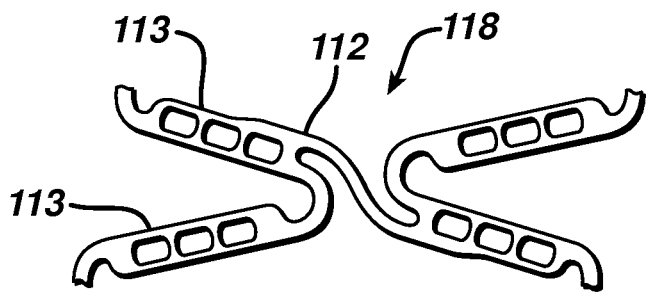
FIG. 6J is a close-up plan view of a circular hinge region from a flexible stent according to one embodiment of the present invention.
Figure 6K:
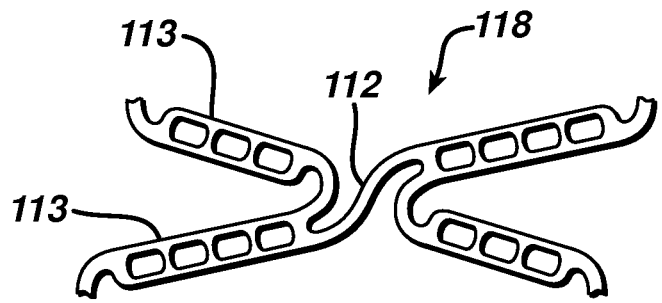
FIG. 6K is a close-up plan view of a circular hinge region from a flexible stent according to one embodiment of the present invention.
Figure 6L:
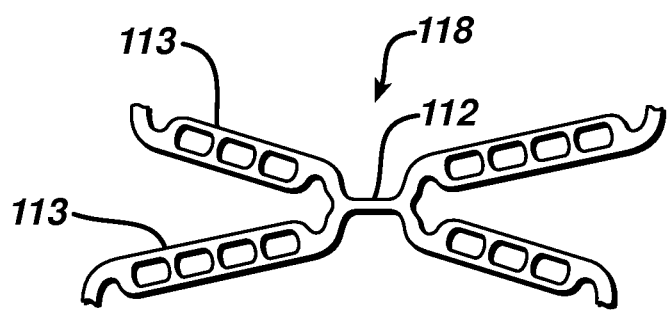
FIG. 6L is a close-up plan view of a circular hinge region from a flexible stent according to one embodiment of the present invention.
Figure 6M:
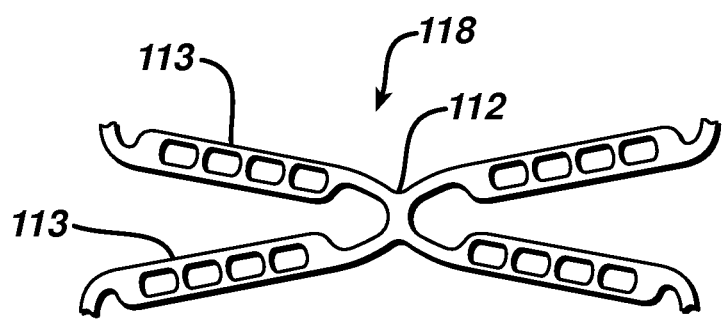
FIG. 6M is a close-up plan view of a circular hinge region from a flexible stent according to one embodiment of the present invention.

FIG. 6A provides greater detail of the "circular hinge region" 118 that serves as a connection point between two strut pairs on adjacent windings of the helical section 108. This hinge region 118 includes several components, and provides a ductile region in between circumferentially adjacent struts 113 that form a strut pair, while providing the necessary connectivity between longitudinally adjacent strut pairs by the flexible connector 112. When combined, the longitudinally adjacent strut pairs and interconnecting flexible connector 112 create regions known as "quad hinge regions". These regions are comprised of four struts that are directly or indirectly connected through the circular hinges 114b and flexible connectors 112. The incident angle, hinge 114b width, degree of taper, length, and hole pattern are subject to change based on the stents intended design, the location of the feature and stent performance optimization. FIGS. 6B through 6M illustrated various connectors 112 that can be use to connect adjacent strut pairs in the circular hinge region 118.

Figure 7:
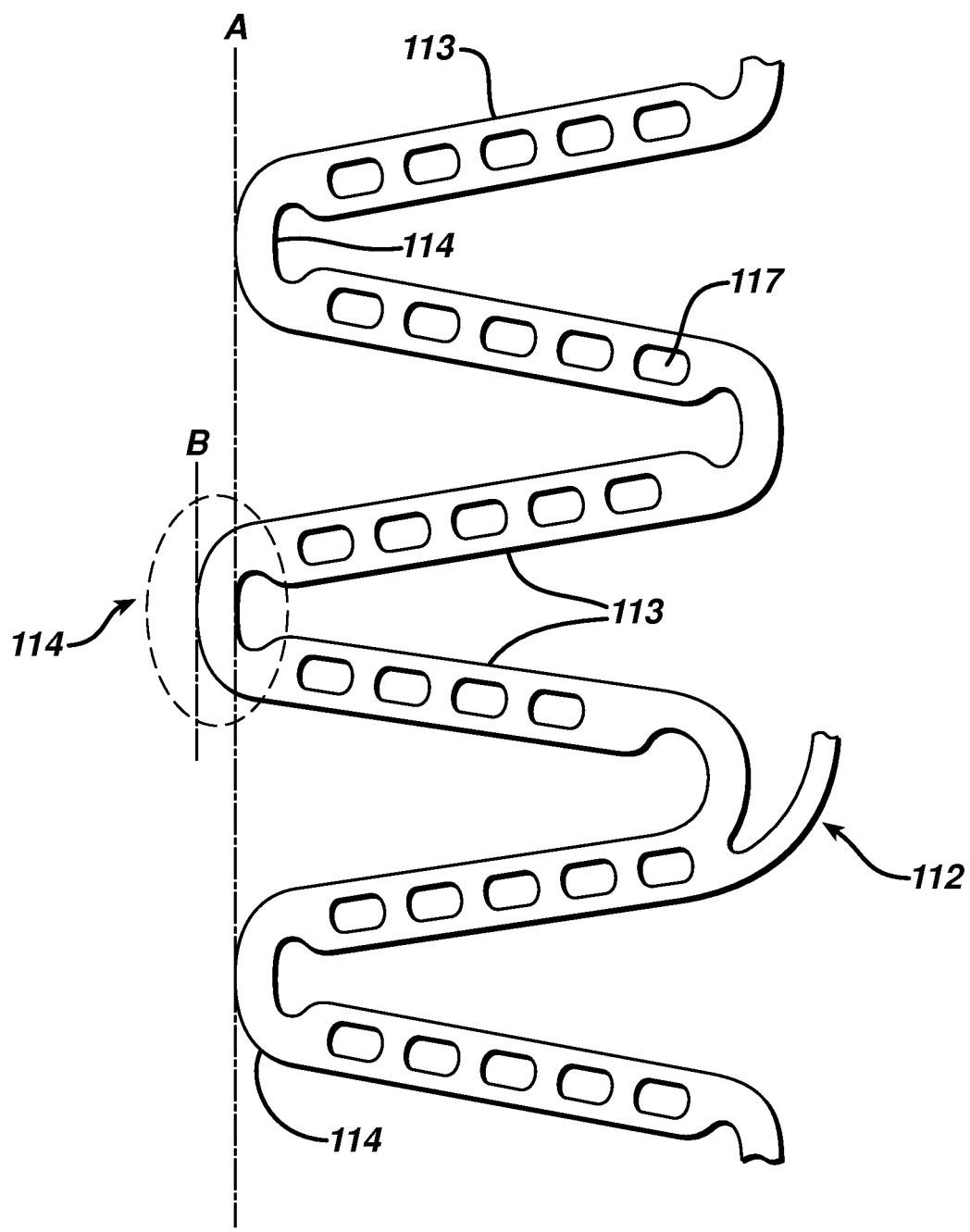
FIG. 7 is a close-up plan view of an index hinge from a flexible stent according to one embodiment of the present invention.

FIG. 7 illustrates another key stent attribute important during the manufacturing process of the stent 100. The encircled ductile hinge 114 is known as the "index hinge". This "index hinge" is characterized by longer strut 113 lengths, which causes the ductile hinge or strut 113 head to protrude beyond the plane of the strut 113 heads on the remaining struts within the sinusoidal end ring. For ease of illustration, reference line A has been drawn perpendicular to the longitudinal axis 103 and tangent to the curved surfaces of both the hinges 114 above and below the index hinge. Reference line B has been drawn perpendicular to the longitudinal axis 103 and tangent to the curved surface of the hinge 114 representing the index hinge. The distance between reference lines A and B along the longitudinal axis is the offset provided by the index. This offset serves as a reference point to help determine the orientation of the stent 100. The "index hinge" may occur at any location along the proximal and distal ring-like end sections 106, 107.

Generally speaking, the ductile hinges 114 are deformable elements that are substantially thinner in width than the surrounding struts 113. This allows the ductile hinges 114 to sustain plastic deformation while still remaining flexible in the deformed state. The struts 113 are therefore much stiffer than the ductile hinges 114, and thus do not experience any plastic deformation during stent expansion. The struts 113 essentially rotate as rigid bodies, while the ductile hinges 114 are designed to the bear the plastic strains associated with stent expansion. As a result, the depots 117 in the struts 113 are shielded from undue stress during expansion that may cause damage or dislodgement of the agents and/or polymer inlays. The depots 117 are ideally in a stress-free state throughout the stent deployment process.

In a preferred embodiment of the present invention, the ductile hinges 114 are optimized, through the use of width tapering, such that they offer sufficient radial stiffness to the stent 100 while simultaneously ensuring that peak plastic strains at full expansion do not exceed the strain carrying capability of the material. This width tapering is optimized, for each hinge 114 type, to achieve a smooth and uniform distribution of plastic strains along the length of the ductile hinge 114. By smoothing the strain distribution and thus eliminating strain concentrations in the ductile hinge 114, the width, and thereby stiffness, is maximized. Maximizing the stiffness of the ductile hinge 114 is advantageous in providing radial stiffness and fatigue durability for the stent 100.

In general the width of the tapered ductile hinge 114 gradually increases while approaching the root of the hinge 114, where the hinge 114 meets an abrupt transition into the wider strut 113 (or stiffer structure). This prevents plastic strains from concentrating at the roots of the hinges since the tapered hinge root is stiffer and therefore distributes plastic strain to the central portion of the hinge 114. The central portion of the ductile hinge 114, which encompasses the apex of the curve, generally has a uniform width. Turning again to FIGS. 2 and 3, the ring-like end sections 106, 107 include a plurality of circumferentially arranged, longitudinally oriented strut members 113 connected at opposite ends by a plurality of circumferentially oriented ductile hinges 114 in a substantially sinusoidal S or Z shaped pattern so as to form the band into an endless ring. In the illustrated embodiment, the end sections 106, 107 are formed from struts 113 of varying length as needed optimize the stent design and provide the necessary geometry for the connection at the anchor point where the interior helical section 108 is first connected to the ring-like end sections 106, 107.

Between the ring-like end sections 106, 107 lies the interior helical section 108 of the stent 100, where the band of sinusoidally arranged struts 113 and hinges 114 follow a helical path. The helical band of the interior section 108 is achieved by arranging the struts 113 in a repeating pattern of alternating short and long lengths. The helical interior section 108 may be further divided into proximal and distal transition zone 109, 110 respectively, and a central zone 111.

The central zone 111 comprises strings (collections of elements) formed from groups of contiguous strut members 113 and hinge members 114 organized to form a string pattern. In one embodiment of the invention, contiguous strings have different string patterns and repeating strings are geometrically symmetric to form a repeating central pattern. In a preferred embodiment of the invention, the repeating central pattern consists of two different repeating strings. The central zone 111 therefore has a constant pitch and incident angle.

As used herein the term pitch is understood to mean the number of sinusoidal turns over a given area. This is similar nomenclature to the diametral pitch of a gear. The greater the pitch, the greater the number of sinusoidal turns, i.e. the greater number of struts 113 and ductile hinges 114, will be found per wrap as the sinusoidal band winds about the longitudinal axis 103. This creates a very dense pattern of struts 113 and hinges 114. Conversely, the smaller the pitch, the smaller number of sinusoidal turns, and thus the smaller number of struts 113 and hinges 114 will be found per wrap as the sinusoidal band winds about the longitudinal axis 103. The term incident angle refers specifically to the helical winding section of the stent 100 and is understood to mean the angle at which the sinusoidal band makes (wraps) with the longitudinal axis.

Figure 8:
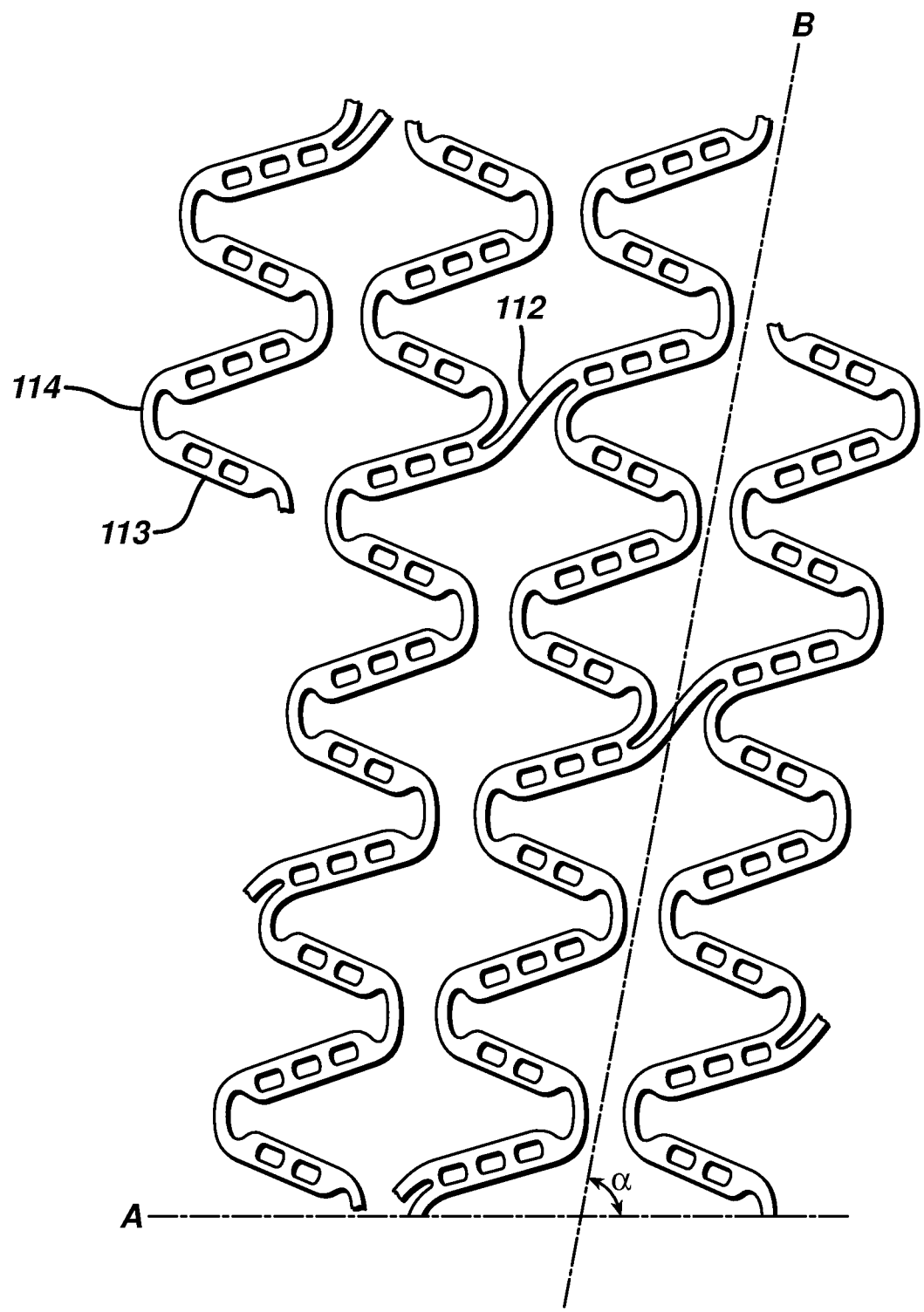
FIG. 8 is a close-up plan view of the central zone depicted in FIG. 3 to illustrate the incident angle of the helical band (wrap).

FIG. 8 is a close up 2 dimensional view of the central zone 111 depicted in FIG. 3. A first reference line "A" has been drawn parallel to the longitudinal axis 103. A second reference line "B" has been drawn to represent the direction of the sinusoidal band. The incident angle ($\alpha$) is the angle between reference line A and reference line B.

Figure 9A:
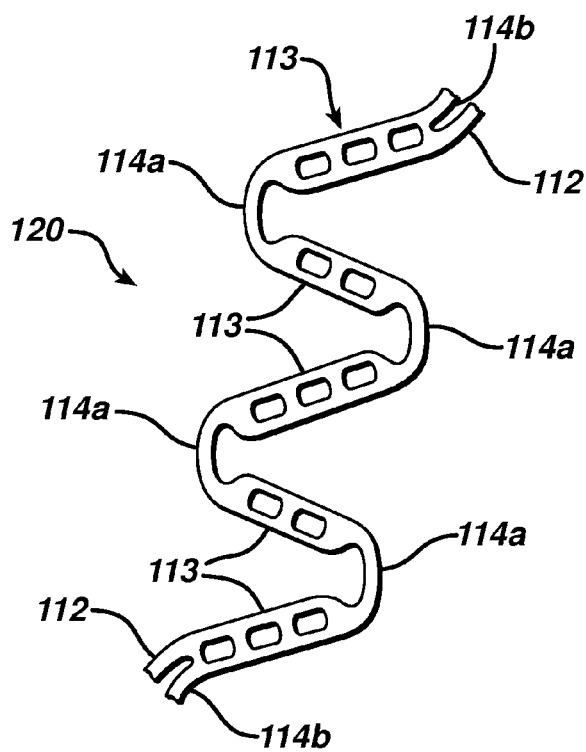
FIG. 9A is a close-up plan view of a connector strut string that is part of the repeating pattern that forms the central zone of the flexible stent illustrated in FIG. 2 according to one embodiment of the present invention.
Figure 9B:
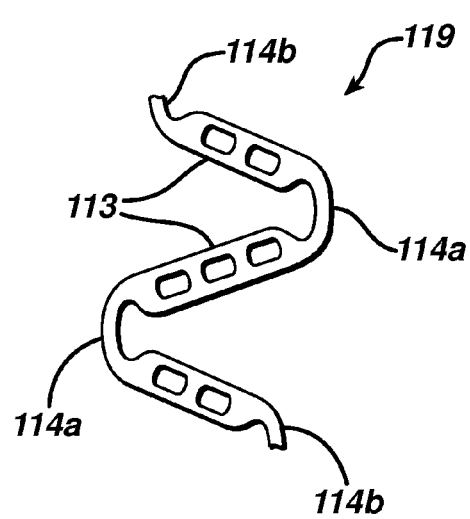
FIG. 9B is a close-up plan view of a free strut string that is part of the repeating pattern that forms the central zone of the flexible stent illustrated in FIG. 2 according to one embodiment of the present invention.

FIGS. 9A and 9B illustrate the two strut strings that are part of the repeating pattern that form the central zone 111 of the stent 100 according to one embodiment of the present invention. Referring to FIGS. 3, 8, 9A and 9B, the central zone 111 starts at the proximal end of the distal transition zone 110 with a free strut string 119 illustrated in FIG. 9B. The illustrated free strut string 119 includes a long three depot strut 113 connected on each end to a short two depot strut 113 by a free hinge 114a. The free strut string 119 is attached on its proximal end to the distal end of a connector strut string 120. The connector strut string 120 includes a connector hinge 114b at its proximal and distal ends, and an alternating arrangement of three long (three depot) struts 113 and two short (two depot) struts 113 connected by free hinges 114a. This pattern of alternating free strut strings 119 and connector strut strings 120 continue until the central zone 111 meets the proximal transition zone 109. The embodiment illustrated in FIG. 3 has a central zone that includes five free strut strings 119 and four connector strut strings 120. The length of the stent 100 can be changed by adding or shortening the central zone 111, i.e. by adding or removing free strut strings 119 or connector strut strings 120 as necessary to maintain the repeating pattern, while maintaining the proximal and distal transition zones 109, 110, and proximal and distal ring-like end section 106, 107 as disclosed.

The proximal and distal transition zones 109, 110 are sections of variable pitch, and in which there is no repeatability or symmetry. The proximal and distal transition zones 109, 110 are constructed so as to afford a gradual decrease in pitch in transitioning between the central zone 111 and the proximal and distal ring-like end sections 105, 107. The proximal and distal transition zones 109, 110 are connected to the proximal and distal ring-like end section 106, 107, respectively, by a connecting geometry called an anchor hinge.

The stent 100 designs depicted in the aforementioned figures are known as an open cell design, meaning that connectors between longitudinally adjacent windings of sinusoidal elements occur only intermittently through the structure rather than spanning every longitudinally adjacent hinge 114 or strut 113. A design in which every longitudinally adjacent hinge or strut is connected is known as a closed cell design. An open-celled architecture is generally more flexible than a closed-cell architecture.

As previously described, the general architecture of the stent 100 includes a helical interior section 108 with ring-like end sections 106, 107 at each end, and connectors 112 distributed through the architecture for structural stability under a variety of loading conditions. The helical interior section 108 may be further separated into a central zone 111 having a constant pitch and incident angle, and proximal and distal transition zones 109, 110 respectively. This general architecture remains the same for various stents of different sizes; however, the geometry and pattern of the elements (struts, hinges and flex connectors) may change as need to adapt to various desired stent diameters.

Figure 10:
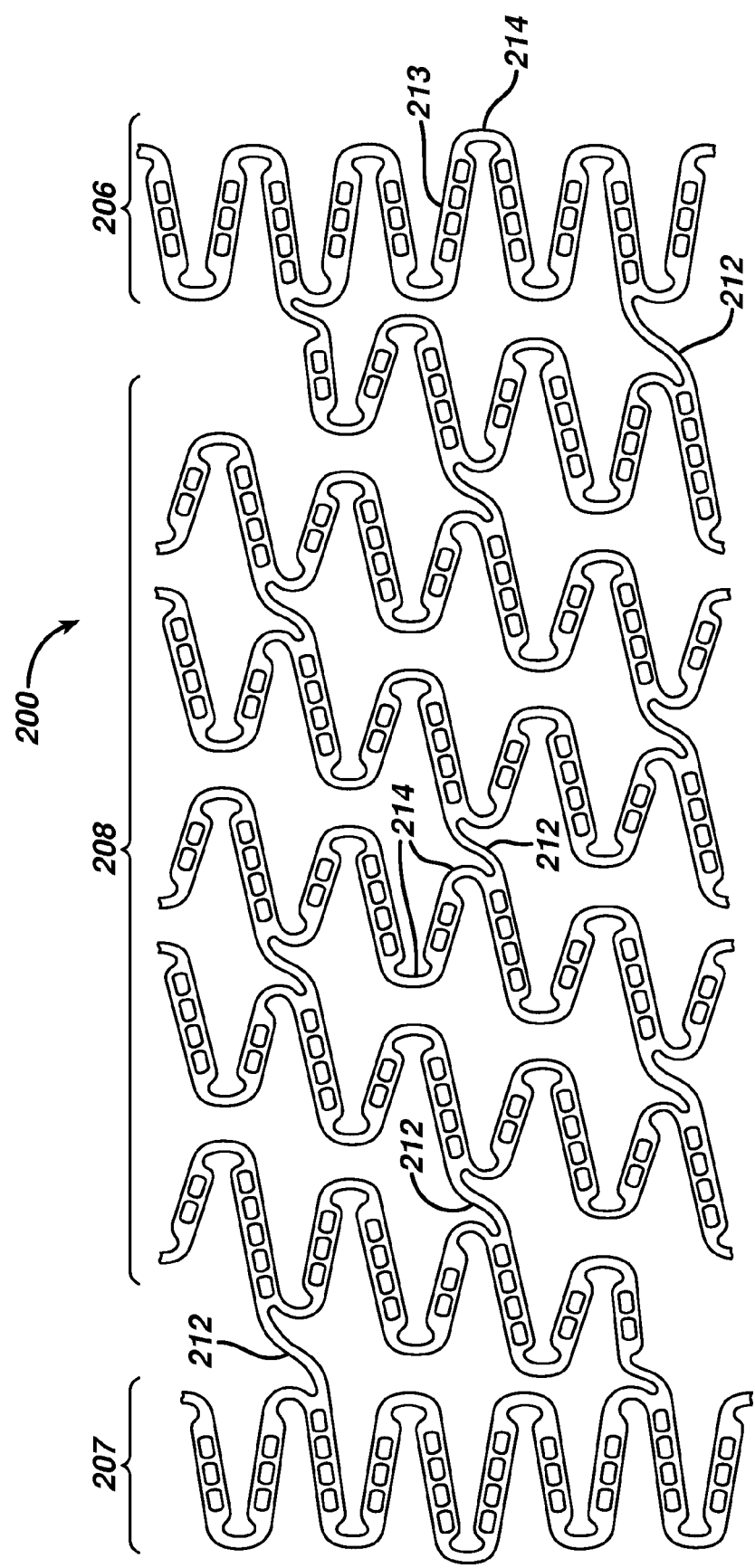
FIG. 10 is a plan view of a flexible stent according to one embodiment of the present invention.
Figure 11:
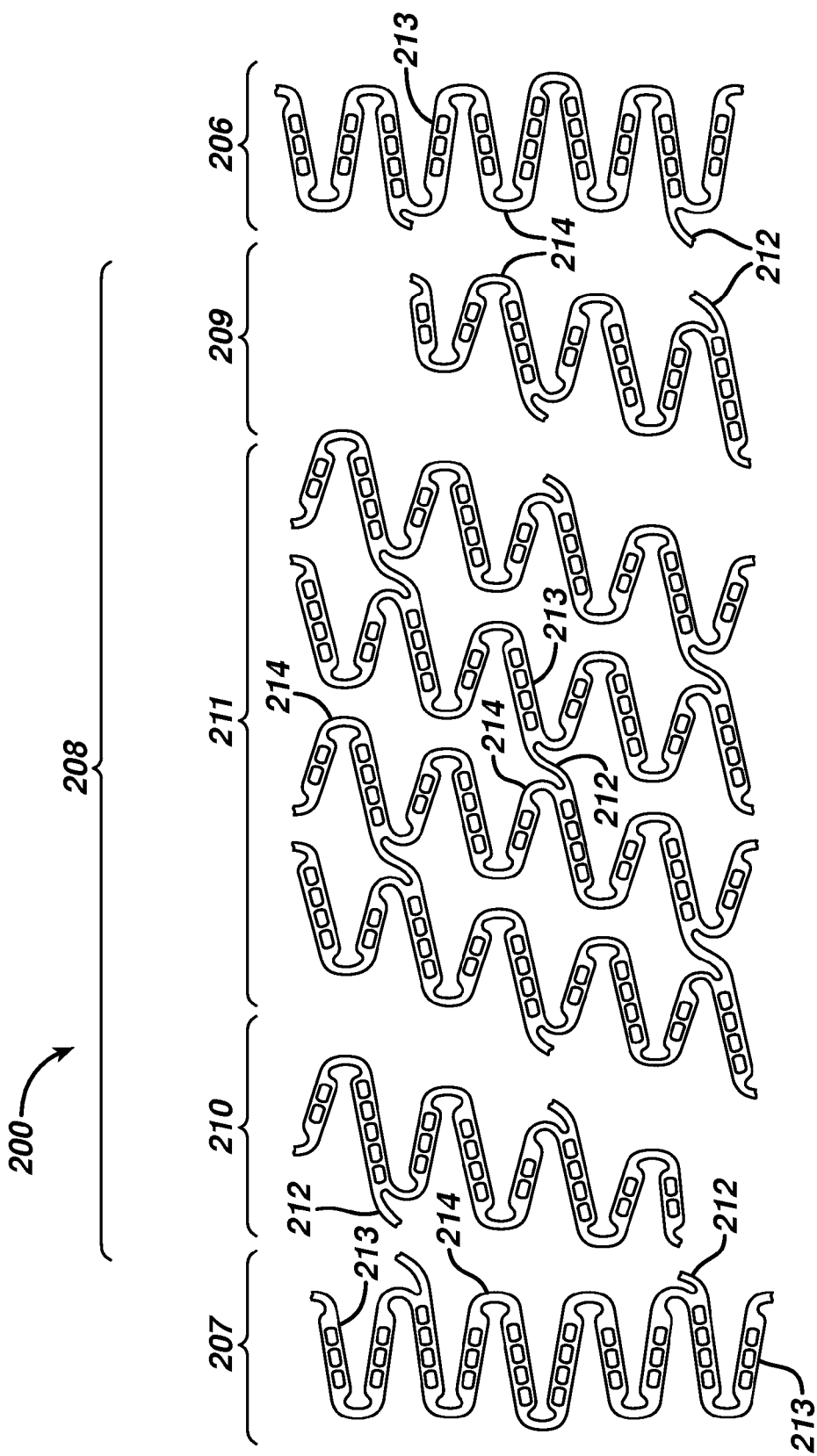
FIG. 11 is an exploded plan view of the flexible stent of FIG. 10.
Figure 12:
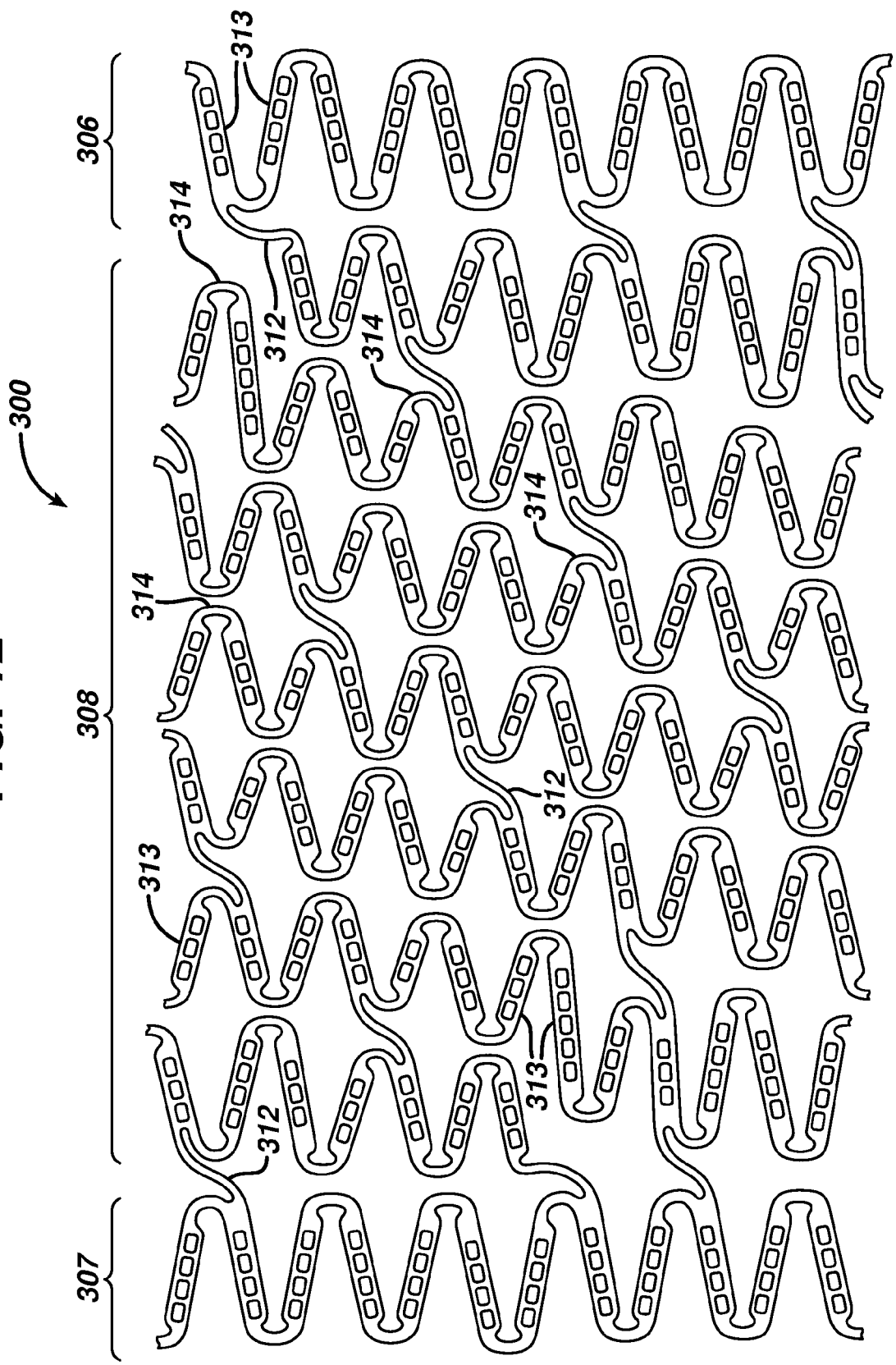
FIG. 12 is a plan view of a flexible stent according to one embodiment of the present invention.
Figure 13:
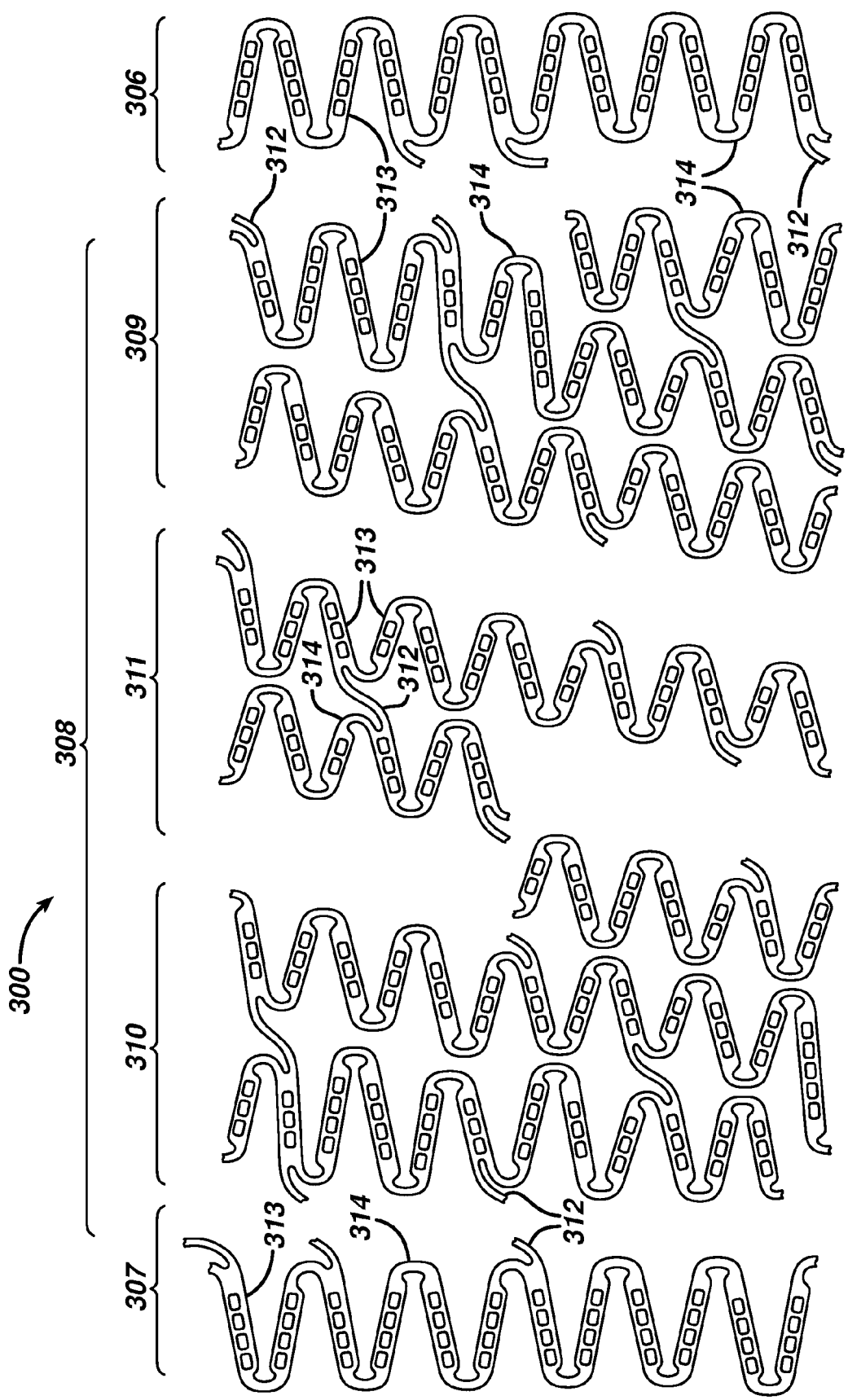
FIG. 13 is an exploded plan view of the flexible stent of FIG. 12.
Figure 14:
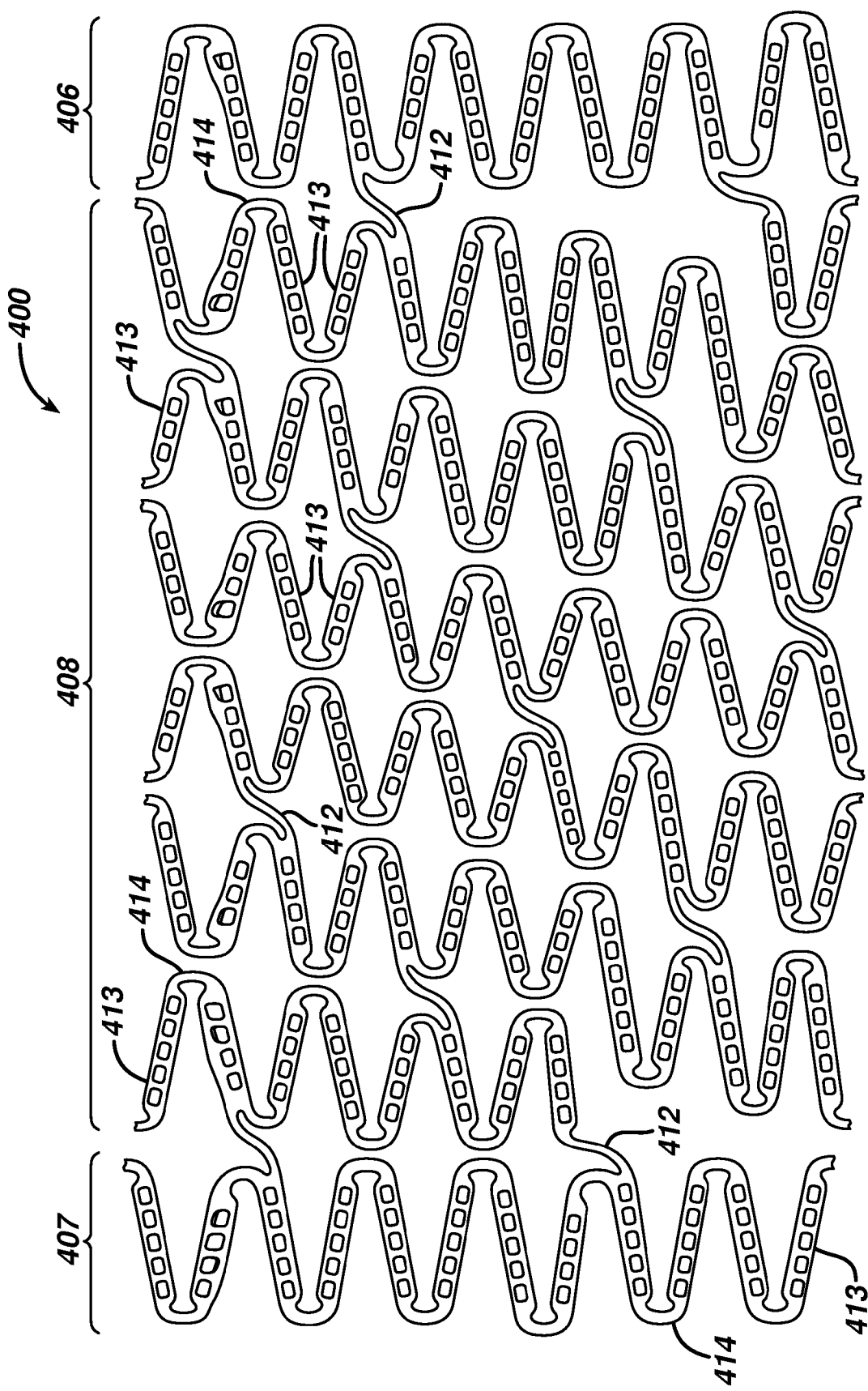
FIG. 14 is a plan view of a flexible stent according to one embodiment of the present invention.
Figure 15:
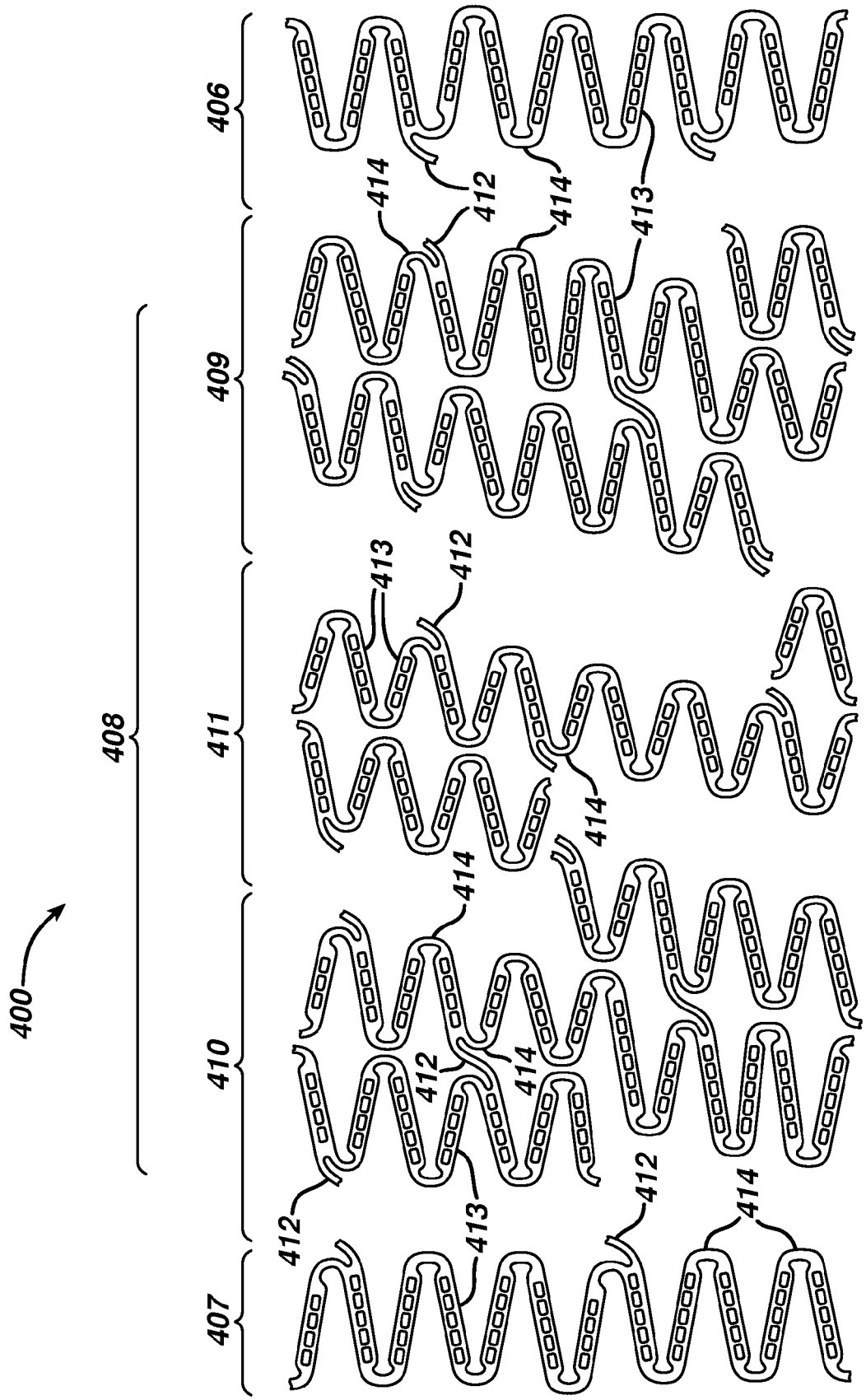
FIG. 15 is an exploded plan view of the flexible stent of FIG. 14.

FIGS. 10 through 15 illustrate various embodiments of the stent designs for different diametrically size stents. FIGS. 10, 12 and 14 are two-dimensional plan views, similar to FIG. 2, illustrating stents 200, 300, 400, respectively, of different sizes and patterns. FIGS. 11, 13 and 15 are exploded plan views, similar to FIG. 3, of the stents 200, 300, 400, respectively, illustrating the different sections and zones. For ease of illustration, like reference numerals have been assigned to like elements of the stent 100, and it is understood that the description of elements related to stent 100 applies equally to like elements in stents 200, 300 and 400.

Each stent pattern design is customized to target optimal results based on the treatment of the stent's intended target vessel. FIGS. 10 and 11 represents one embodiment of a stent 200 intended for extra small diameter target vessel lesions. The extra small diameter stent family has been optimized for very small vessel diameters via several design features, and is meant to be fabricated from a smaller diameter tubing material.

The current embodiment for an extra small stent includes sinusoidal proximal and distal ring-like end sections 206, 207 comprised of ten struts 213 in each ring-like end sections 206, 207. Between the ring-like end sections 206, 207 lies the interior helical section 208 of the stent 200, where the sinusoidal arrangement of struts 213 and hinges 214 follow a helical path. The helical path of the interior section 208 is achieved by arranging the struts 213 in a repeating pattern of alternating short and long lengths to form a band. There are nine struts 213 per winding in each the interior bands. The fewer number of struts allows for increased stent performance while maintaining critical processing parameters. The helical interior section 208 may be further divided into proximal and distal transition zones 209, 210 respectively and a central zone 211 as illustrated in FIG. 11.

The central zone 211 consists of repeating strut strings, or collections of struts, which are geometrically symmetric to form a repeating pattern in the band. The central zone 211 therefore has a constant pitch and incident angle. The repeating interior pattern is comprised of two 3-strut patterns that alternate to form the 9-strut repeating interior pattern.

Figure 18:
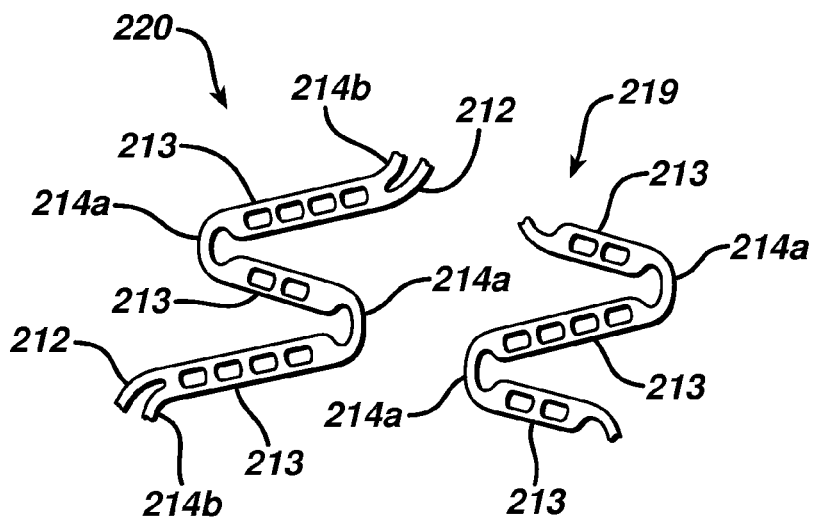
FIG. 18 is a close-up plan view of the free strut string and the connector strut string that are part of the repeating pattern that form the central zone of the flexible stent illustrated in FIG. 10 according to one embodiment of the present invention.

FIG. 18 illustrates the two strut strings 219, 220 that are part of the repeating pattern from the central zone 211 of the stent 200 according to one embodiment of the present invention. Referring to FIGS. 10, 11 and 18, the central zone 211 starts at the distal end of the proximal transition zone 209 with a free strut string 219 illustrated in FIG. 18. The illustrated free strut string 219 includes a long (four depot) strut 213 connected on each end to a short (two depot) strut 213 by a free hinge 214a. The free strut string 219 is attached on its distal end to the proximal end of a connector strut string 220. The connector strut string 220 includes a connector hinge 214b at its proximal and distal ends, and an alternating arrangement of two long (four depot) struts 213 and one short (two depot) strut 213 connected by free hinges 214a. This pattern of alternating free strut strings 219 and connector strut strings 220 continue until the central zone 211 meets the distal transition zone 210. The embodiment illustrated in FIGS. 10 and 11 have a central zone that includes six free strut strings 219 and six connector strut strings 220.

The current embodiment for a medium sized stent includes sinusoidal proximal and distal ring-like end sections 306, 307 comprised of twelve strut 313 end rings. Between the ring-like end sections 306, 307 lies the interior helical section 308 of the stent 300, where the sinusoidal arrangement of struts 313 and hinges 314 in the band follow a helical path. The helical path of the interior section 308 is achieved by arranging the struts 313 in a repeating pattern of alternating short and long lengths to form the band. There are thirteen struts 313 per band winding in the interior helical section 308. The increased number of struts allows for increased stent performance while maintaining critical processing parameters. The helical interior section 308 may be further divided into proximal and distal transition zones 309, 310 respectively and a central zone 311 as illustrated in FIG. 13.

The central zone 311 consists of repeating strut strings, or collections of struts, which are geometrically symmetric to form a repeating pattern. The central zone 311 therefore has a constant pitch and incident angle. The repeating interior pattern is comprised of one 3-strut pattern and one 5-strut pattern that alternate to form the 13-strut repeating interior pattern.

Figure 17:
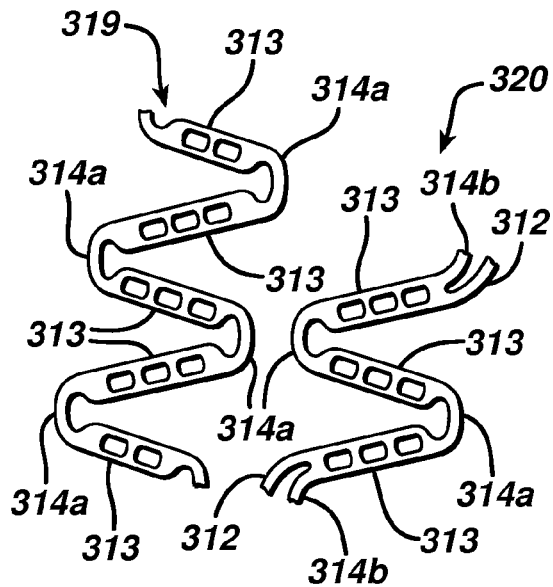
FIG. 17 is a close-up plan view of the free strut string and the connector strut string that are part of the repeating pattern that form the central zone of the flexible stent illustrated in FIG. 12 according to one embodiment of the present invention.

FIG. 17 illustrates the two strut strings 319, 320 that are part of the repeating pattern forming the central zone 311 of the stent 300 according to one embodiment of the present invention. Referring to FIGS. 12, 13 and 17, the central zone 311 starts at the distal end of the proximal transition zone with a connector strut string 320 illustrated in FIG. 17. The illustrated connector strut string 320 includes a connector hinge 314b at its proximal and distal ends, and an arrangement of three long (three depot) struts 313 connected by free hinges 314a. The free strut string 319 is attached on its proximal end to the distal end of the connector strut string 320. The illustrated free strut string 319 includes a series of three long (three depot) struts 313 interconnected by a free hinge 314a. The three, three depot struts 313 are connected on each end to a short two depot strut 313 by free hinges 314a. The pattern of alternating connector strut strings 320 and free strut strings 319 continue until the central zone 311 meets the distal transition zone 310. The embodiment illustrated in FIGS. 12 and 13 has a central zone that includes three connector strut strings 320 and two free strut strings 319. The length of the stent 300 can be changed by adding or shortening the central zone 311, i.e. by adding or removing connector strut strings 320 or free strut strings 319 as necessary to maintain the repeating pattern, while maintaining the proximal and distal transition zones 309, 310 and proximal and distal ring-like end section 306, 307 as disclosed.

FIGS. 14 and 15 represents one embodiment of a stent 400 intended for a large diameter target vessel lesions. The large diameter stent family has been optimized for larger vessels via several design features. Like previous designs, the current embodiment contains sinusoidal proximal and distal ring-like end sections 406, 407 comprised of twelve struts 413. The struts 413 in said end sections 406, 407 are of varying length; however, on the whole they are longer in the large diameter stent design than the typical strut of an equivalent smaller nominal stent design. The end sections 406, 407 are connected via several points to the proximal and distal transition zones 409, 410 as illustrated in FIG. 15.

Figure 16:
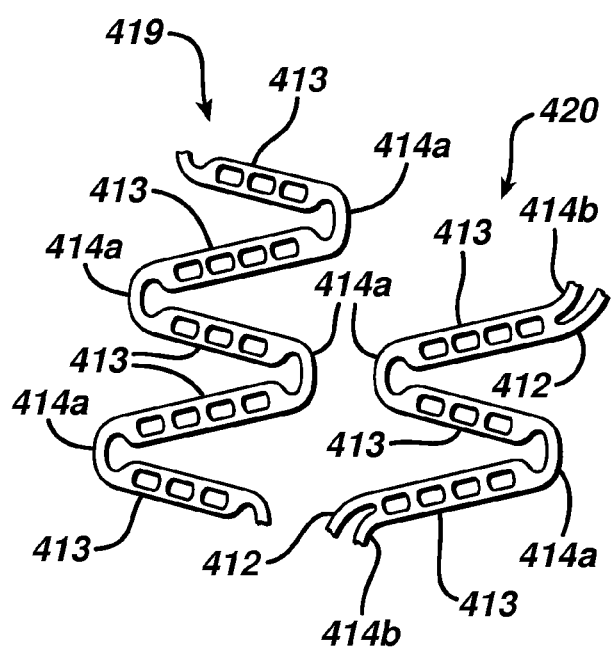
FIG. 16 is a close-up plan view of the free strut string and the connector strut string that are part of the repeating pattern that form the central zone of the flexible stent illustrated in FIG. 14 according to one embodiment of the present invention.

FIG. 16 illustrates the two strut strings that are part of the repeating pattern from the central zone 411 of the stent 400 according to one embodiment of the present invention. Referring to FIGS. 14, 15 and 16, the central zone 411 starts at the proximal end of the distal transition zone 410 with a free strut string 419 illustrated in FIG. 16. The illustrated free strut string 419 includes an alternating arrangement of short (three depot) struts 413 and long (four depot) struts (413) interconnected on each end by a free hinge 414a. The free strut string 419 is attached on its proximal end to the distal end of a connector strut string 420. The connector strut string 420 is three struts 413 long, and includes a connector hinge 414b at its proximal and distal ends. The three struts in the connector string 420 include an alternating arrangement of long (four depot) struts 413 and a short (three depot) strut 413 connected by free hinges 414a. This pattern of alternating free strut strings 419 and connector strut strings 420 continue until the central zone 411 meets the proximal transition zone 409. The embodiment illustrated in FIG. 15 has a central zone that includes three free strut strings 419 and two connector strut strings 420.

Figure 19:
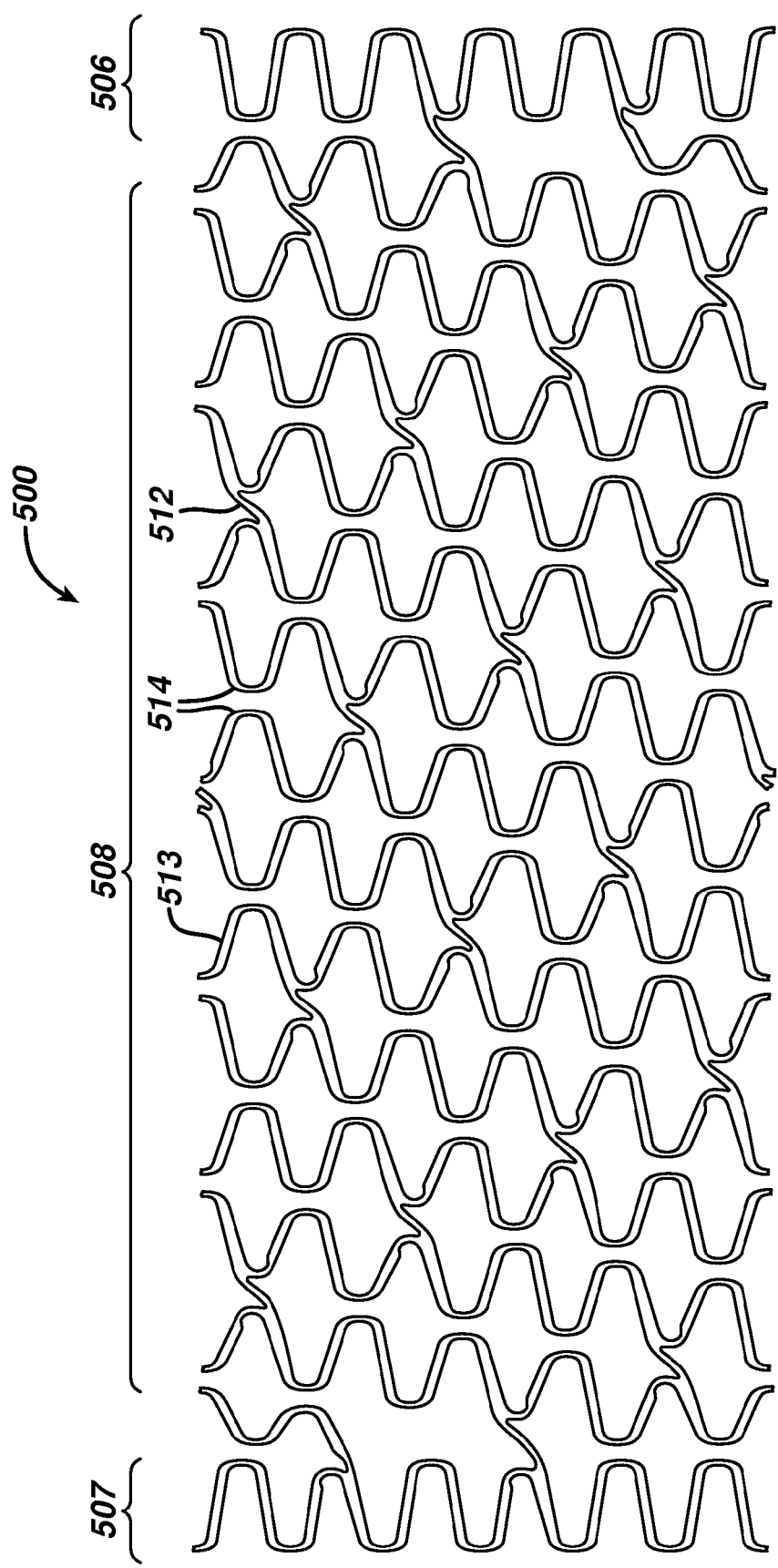
FIG. 19 is a plan view of a flexible stent without depots according to one embodiment of the present invention.

The present invention also contemplates the use of solid struts in similar strut/hinge orientations as those disclosed in FIGS. 2, 10, 12, and 14. FIG. 19 illustrates a stent 500 having similar design architecture without depots along the struts 513. Stent 500 can be used as a bare metal stent or can be partially or completely coated with an agent and/or appropriate carrier as is known in the art.

Stents 100 through 500 previously depicted and described have helical interior sections 108, 208, 308, 408 and 508 respectively, of repeating longitudinally oriented struts connected by a series of circumferentially oriented ductile hinges in a substantially S or Z shaped sinusoidal-like pattern. As previously described, the helical interior section is formed by the band of sinusoidally arranged struts and hinges that follow a helical path. The helical band of the interior section 108, 208, 308, 408 and 508 is achieved by arranging the struts in a repeating pattern of alternating short and long lengths. The helical interior section 108, 208, 308, 408 and 508 may be further divided into proximal and distal transition zones and a central zone 111, 211, 311, 411, 511 respectively.

The central zones comprise strings (collections of elements) formed from groups of contiguous strut members and hinge members organized to form a string pattern. In one embodiment of the invention, contiguous strings have different string patterns and repeating strings are geometrically symmetric to form a repeating central pattern. In a preferred embodiment of the invention, the repeating central pattern consists of two different repeating strings. The central zone therefore may have a constant pitch and incident angle. Complimentary elements forming the strings and string patterns, i.e. struts and hinges in like strings, are generally uniform in size and shape.

Another inventive stent design may have one or more structural features along the intermediate section of the helical interior section to effectively interrupt the repeating central pattern in the interior section, particularly the central zone, to create a central zone with two separate helical subsections of repeating patterns, one before and one after the structural feature.

The structural feature may add more structure to the stent while retraining overall stent flexibility. When a balloon is used to mechanically expand the stent, the feature may also provide additional securement of the stent on the balloon, and reduce the risk of fore lengthening—the unintentional axial stretching the open cell design as a result of deployment. The condition is particularly prevalent if the balloon moves or pulls one end of the stent.

The structural feature may be centered along the helical section length, effectively bisecting the intermediate section into two equal subsections. Centering the structural feature offers the opportunity for symmetry of the stent, simplifying design and modeling, and allowing stent properties to remain more uniform. However, the structural feature does not need to be centrally located with the intermediate helical section, and this design should not unnecessarily limit the scope of this invention.

Various embodiments of the present invention having a structural feature are illustrated in the following figures. Like reference numerals are used to indicate similar features and elements between the featured stent and stents 100 through 500 previously described. For example, strut 113 in stent 100 is similar to strut 1113 in stent 1100.

Figure 20:
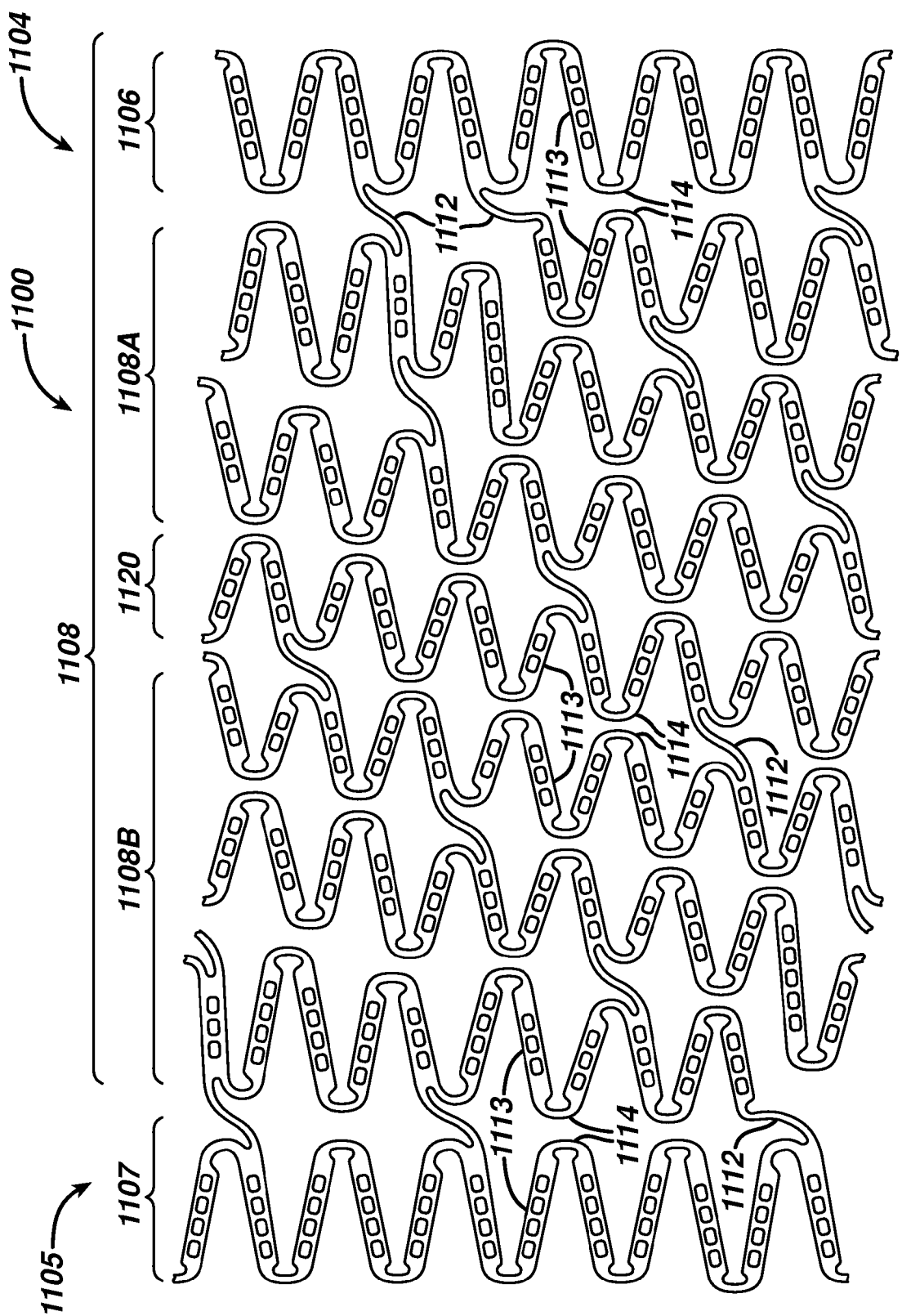
FIG. 20 is a plan view of a flexible stent according to one embodiment of the present invention.
Figure 21:
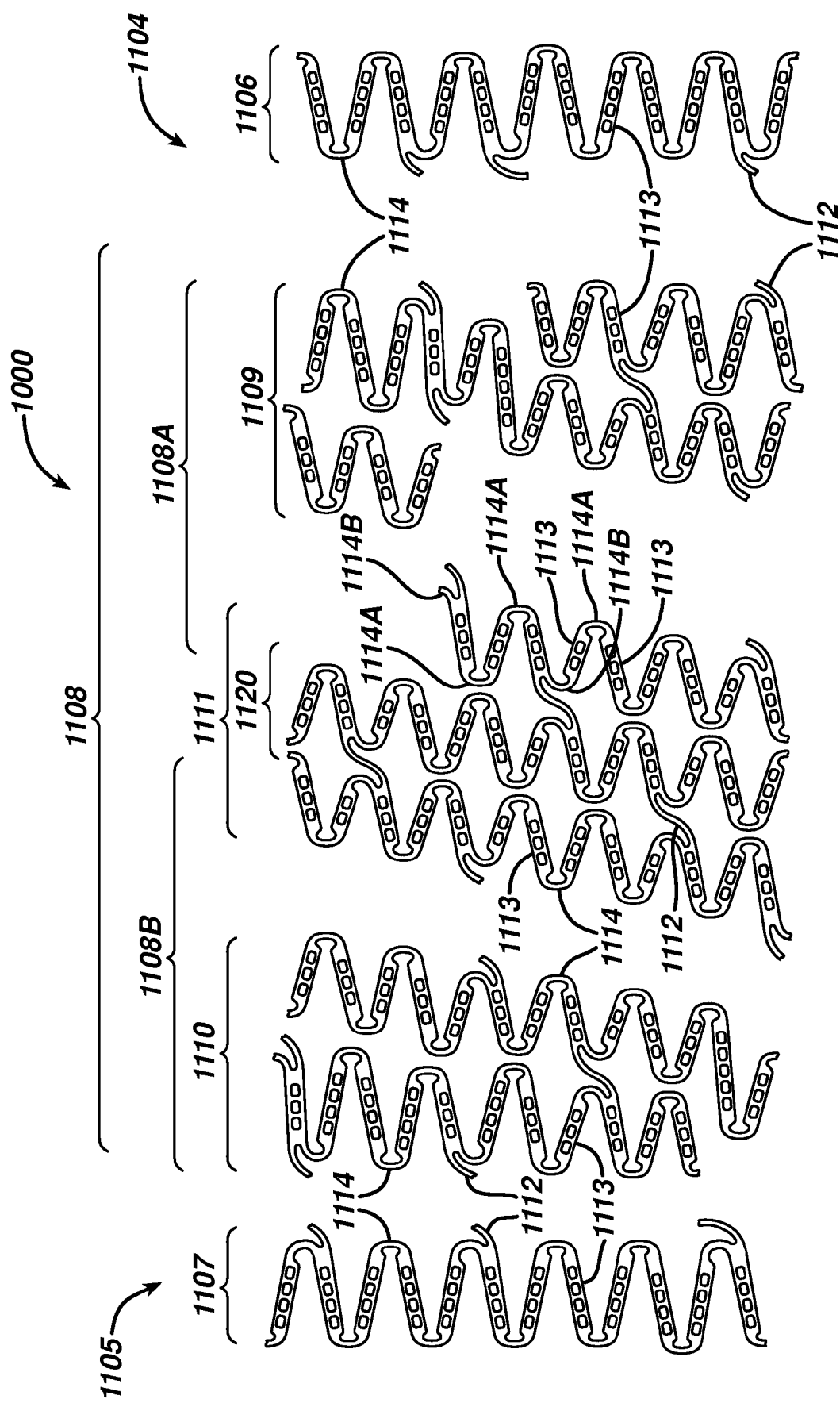
FIG. 21 is an exploded plan view of the flexible stent of FIG. 20.

FIGS. 20 and 21 are plan views of a stent 1100 in a partially expanded condition according to one embodiment of the present invention. The stent architecture generally includes proximal and distal closed ring-like end sections 1106, 1107 along the proximal and distal ends 1104, 1105 respectively, and a substantially helical interior section 1108 there between. The stent 1100 includes a plurality of longitudinally oriented struts 1113 connected by a series of circumferentially oriented ductile hinges 1114. Circumferentially adjacent struts 1113 are connected at opposite ends by the hinges 1114 in a substantially S or Z shaped sinusoidal-like patter to form a band. Flexible connectors 1112 are distributed through the stent 1100 architecture for structural stability under a variety of loading conditions. The stent design illustrated in FIGS. 20 and 21 has a flexible connector geometry, however a wide variety of connectors geometries are contemplated. See generally FIGS. 6B through 6H.

A structural feature 1120 is located along the interior section 1108, functionally interrupting the helical pattern and effectively segregating the helical interior section 1108 into two separate subsections 1108A and 1108B. In the illustrated embodiment, the structural feature 1120 includes a helical band element 1120 having wider elements at coincident points along the element profile than the remainder of the helical section 1108. A coincident point would be the same relative point on a similar element. For example, the strut width measurement at the midpoint along the longitudinal length of a 3 depot strut in the helical band element 1120 would be wider than the strut width measurement at the midpoint along the longitudinal length of a 3 depot strut that is not in the helical band element 1120. In particular, the illustrated embodiment shows a helical band element 1120 having wider hinges 1114 and struts 1113, however, a helical band 1120 having only wider hinges 1114 or struts 1113 is also contemplated by the present invention. This helical band 1120 is stiffer, changing the expansion and flexibility characteristics of the stent. The width, size and shape of the members can be altered to "tune" the stent and achieve the desired characteristics.

The first subsection 1108A is located between the proximal ring like section 1106 and the widened helical band element 1120. The second helical subsection 1108B is located between the distal ring-like end section 1107 and the widened helical band element 1120. The helical interior section 1108 may further include a central zone 1111 and proximal and distal transition zones 1109, 1110 respectively. The transition zones 1109, 1110 transition between the central zones 1111 and the proximal and distal ring-like end sections 1106, 1107 respectively.

The central zone 1111 may include strings (collections of elements) formed from groups of contiguous strut members 1113 and hinge members 1114 organized to form a string pattern. In one embodiment of the invention, contiguous strings have different string patterns and repeating strings, and the elements that make up the string, are geometrically symmetric to form a repeating central pattern. In a preferred embodiment of the invention, the repeating central pattern consists of two different repeating strings. The central zone 1111 also includes the widened helical band element 1120. The structural feature 1120 interrupts the repeating pattern in the central zone 1111, while the remaining repeating pattern of struts and hinges continues before and after the widened helical band element 1120.

FIG. 21 illustrates the two strut strings that are part of the repeating pattern forming the central zone 1111 of the stent 1100 according to one embodiment of the present invention. The central zone 1111 starts at the distal end of the proximal transition zone 1109 with a connector strut string. The illustrated connector strut string includes a connector hinge 1114b at its proximal and distal ends, and an arrangement of three long (three depot) struts 1113 connected by free hinges 1114a. The free strut string, which follows the connector strut string, is attached on its proximal end to the distal end of the connector strut string. The illustrated free strut string includes a series of three long (three depot) struts 1113 interconnected by a free hinge 1114a. The three, three depot struts 1113 are connected on each end to a short two depot strut 1113 by free hinges 1114a. The pattern of alternating connector strut strings and free strut strings continue until the string pattern 1111 meets the structural feature 1120—in the illustrated embodiment the widened helical band element 1120. As previously described, the elements forming the strings and string patterns, i.e. struts and hinges, are generally uniform in size and shape to complimentary elements in like strings and string patterns. However, the structural feature 1120 illustrated in FIGS. 20 and 21 breaks this pattern. While the structural feature 1120 in the illustrated embodiment does maintain the same strut strings and pattern as the remainder of the central zone 1111, the structural feature 1120 is formed from struts and hinges that are wider than the preceding and following strings. As such, the elements that form the structural feature 1120 are not of the same size and shape as the elements that form the remainder of the central zone 1111. The repeating pattern continues after the structural feature 1120 (widened helical band) until the repeating pattern meets the distal transition zone 1110.

Figure 22:
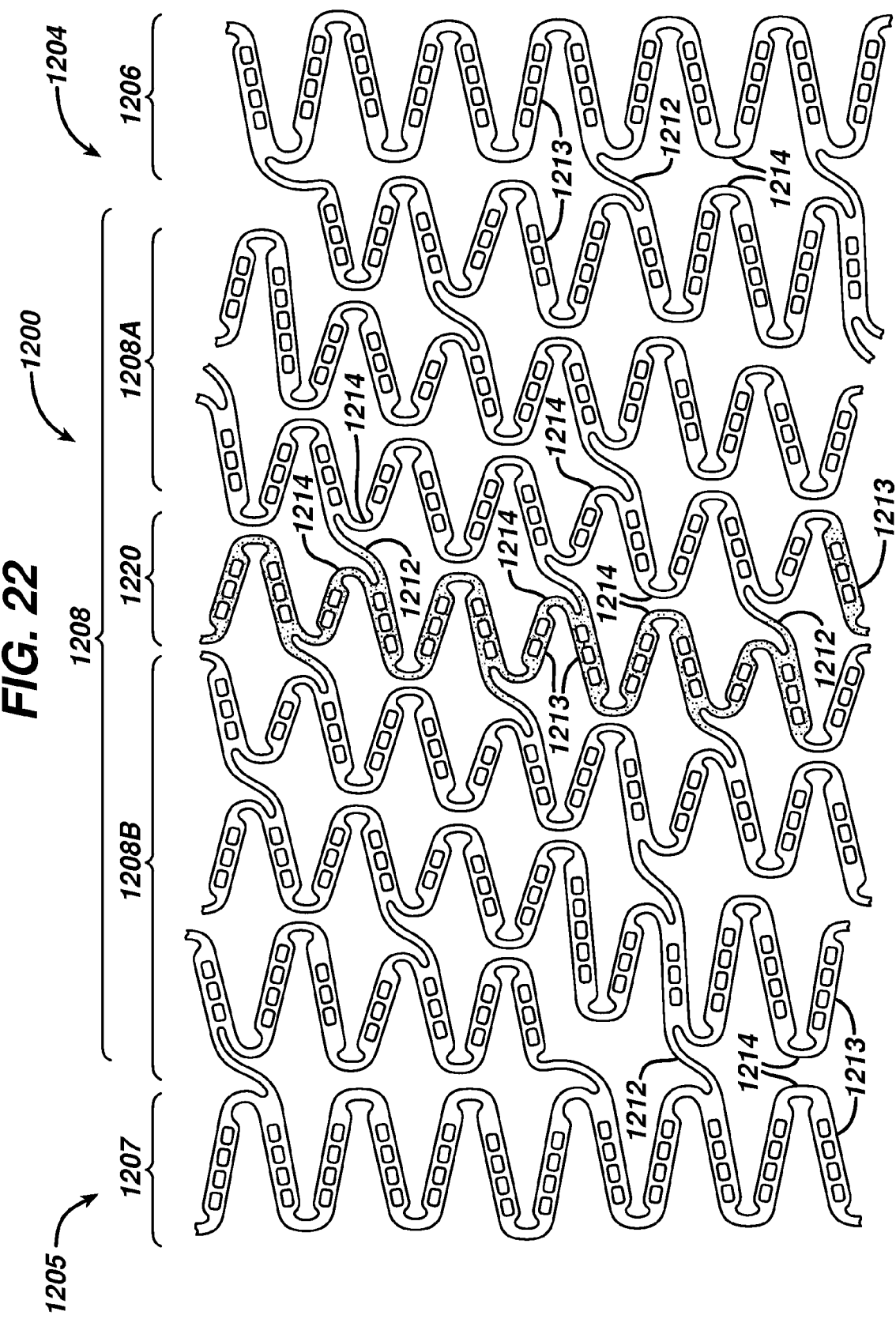
FIG. 22 is a plan view of a flexible stent according to one embodiment of the present invention.
Figure 23:
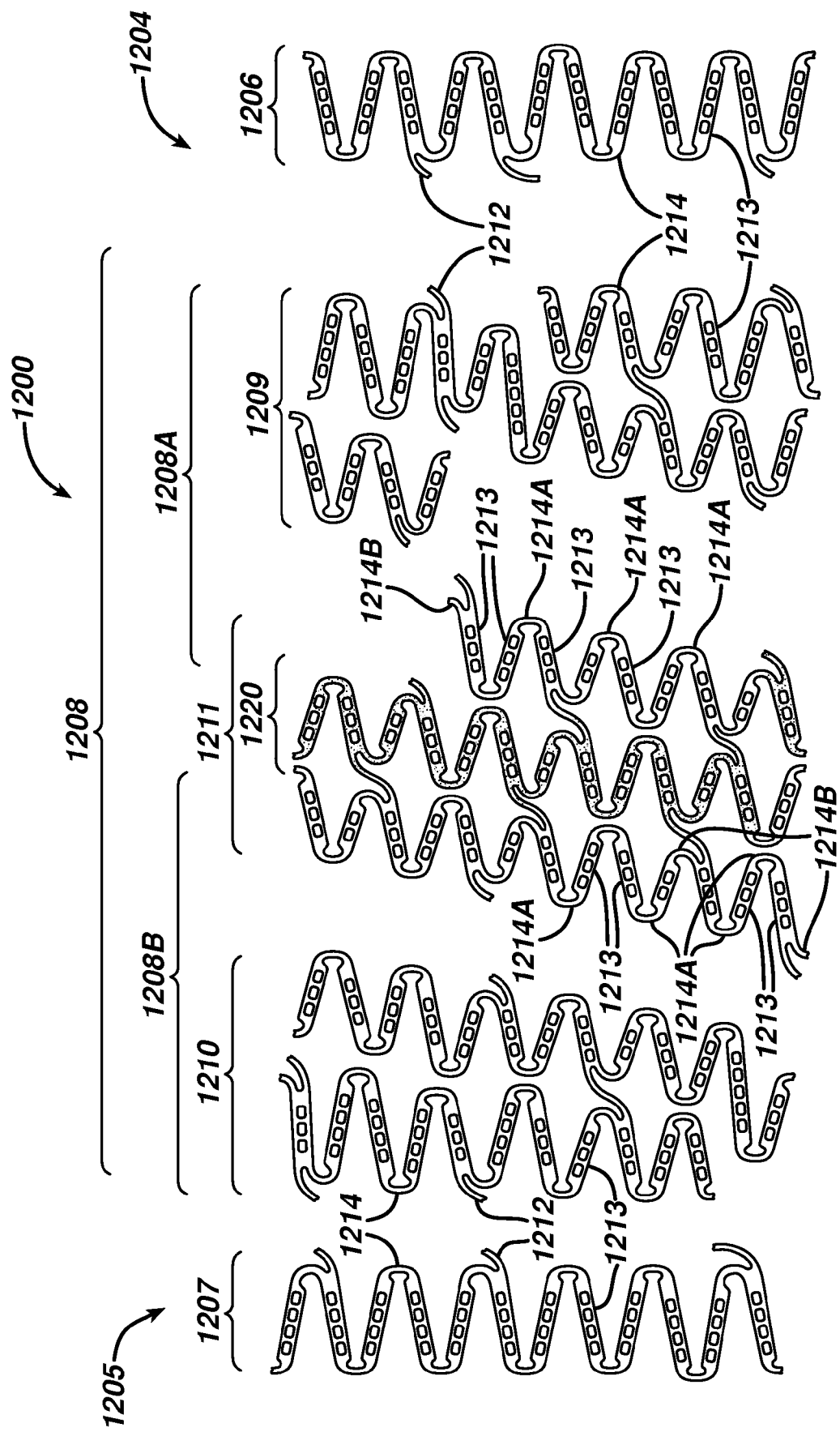
FIG. 23 is an exploded plan view of the flexible stent of FIG. 22.

Another inventive embodiment of a structural feature that interrupts the repeating pattern in the central zone includes a section having additional connectors between adjacent helical windings. FIGS. 22 and 23 are plan views of a stent 1200 in a partially expanded condition according to one such embodiment of the present invention. Similar to stents previously disclosed, the stent 1200 architecture generally includes proximal and distal closed ring-like end sections 1206, 1207 along the proximal and distal ends 1204, 1205 respectively, and a substantially helical interior section 1208 there between. The stent 1200 includes a plurality of longitudinally oriented struts 1213 connected by a series of circumferentially oriented ductile hinges 1214. Circumferentially adjacent struts 1213 are connected at opposite ends by the hinges 1214 in a substantially S or Z shaped sinusoidal-like patter to form a band. Flexible connectors 1212 are distributed through the stent 1200 architecture for structural stability under a variety of loading conditions. To clearly illustrate the structural feature 1220 having additional connectors 1212 reference is made to the connection regions and ductile hinges.

Similar to the stents previously disclosed, there are two types of ductile hinges 1214 found in stent 1200. As described earlier, FIGS. 5A and 5B illustrate the two typical ductile hinges. FIG. 5A represents a single "free hinge" 114a, akin to free hinge 1214a of the present embodiment, which connects two circumferentially adjacent struts 113. In a preferred embodiment, this free hinge 114a is "C" shaped and is substantially symmetric about reference line "A" drawn though the apex point on the curved section. FIG. 5B represents a ductile hinge 114b, akin to hinge 1214b of the present embodiment, that connects two circumferentially adjacent struts 113, where one of the struts is further connected to a flexible connector 112. This ductile hinge 114b is more circular in shape than the "C" shaped free hinge 114a disclosed in FIG. 5A, and is sometimes referred hereto as a "circular hinge" 114b. Although free hinges 1214a and connector hinges 1214b are identified separately here, they are sometimes generally both referred to as ductile hinges 1214. The regions surrounding the circular hinge 1214b is referred to as a circular hinge region. While the flexible connector 1212 and circular ductile hinge 1214b both connect to the same short side of the strut 1213 in the circular hinge region, they are not connected to one another.

Figure 24:
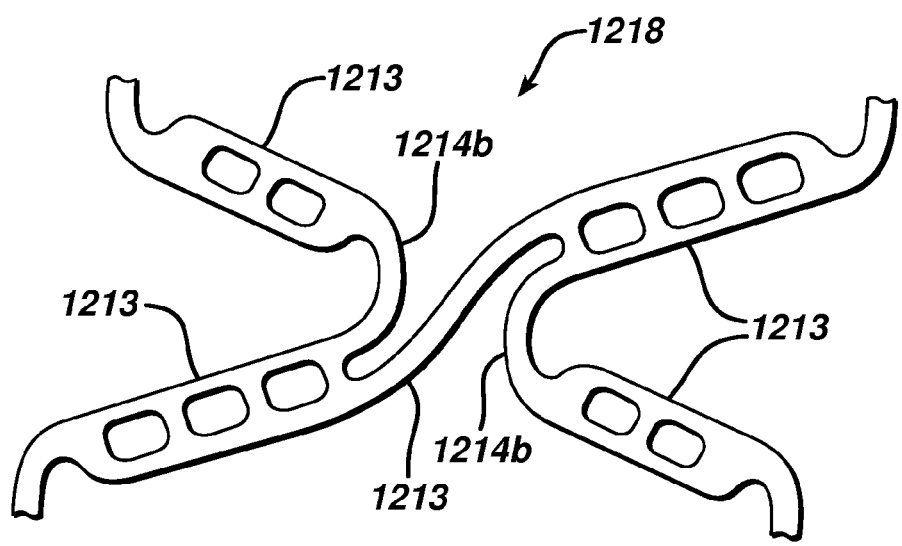
FIG. 24 is a close-up plan view of a circular hinge region from a flexible stent according to one embodiment of the present invention.

FIG. 24 provides greater detail of the "circular hinge region" 1218 that serves as a connection point between two strut pairs on adjacent windings of the helical section 1208. This hinge region 1218 includes several components, and provides a ductile region in between circumferentially adjacent struts 1213 that form a strut pair, while providing the necessary connectivity between longitudinally adjacent strut pairs by the flexible connector 1212. When combined, the longitudinally adjacent strut pairs and interconnecting flexible connector 1212 create regions known as "quad hinge regions". These regions are comprised of four struts that are directly or indirectly connected through the circular hinges 1214b and flexible connectors 1212. The incident angle, hinge 1214b width, degree of taper, length, and hole pattern are subject to change based on the stents intended design, the location of the feature and stent performance optimization. FIGS. 6B through 6M illustrated various connectors that can be use to connect adjacent strut pairs in the circular hinge region 1218. It is the number and spacing between circumferentially adjacent hinge regions 1218 that can be used to identify the structural feature 1220.

The structural feature 1220 is located along the interior section 1208, functionally and structurally interrupting the helical pattern and effectively segregating the helical interior section 1208 into two separate subsections 1208A and 1208B. In the illustrated embodiment, the structural feature 1220 includes a helical band element having a greater number of flexible connectors 1212, i.e. a greater number of circular hinge regions 1218, than the remainder of the interior helical section 1208. That is to say the number and spacing between hinge regions 1218 is greater in the structural feature 1220 region than in the remainder of the stent. For clarity, the helical band element forming the structural feature 1220 having the denser flex connect geometry has been shaded. In particular, the illustrated embodiment shows a structural feature 1220 having flex connectors 1212 connected between hinge regions 1218 at every other circumferentially adjacent strut pair. The additional flex connectors 1212 make the structural feature 1220 stiffer than the remainder of the stent 1200, changing the expansion and flexibility characteristics of the stent. The number and spacing of the flexible connectors 1212 can be altered to "tune" the stent and achieve the desired characteristics. For example, the stent could also have a structural element 1220 where the flex connectors 1212 are connected between every longitudinally adjacent strut pair.

Referring again to FIGS. 22 and 23, the first subsection 1208A is located between the proximal ring like section 1206 and the structural feature 1220. The second helical subsection 1208B is located between the distal ring-like end section 1207 and the structural feature 1220. The helical interior section 1208 may further include a central zone 1211 and proximal and distal transition zones 1209, 1210 respectively. The transition zones 1209, 1210 transition between the central zones 1211 and the proximal and distal ring-like end sections 1206, 1207 respectively.

The central zone 1211 may include strings (collections of elements) formed from groups of contiguous strut members 1213 and hinge members 1214 organized to form a string pattern. In one embodiment of the invention, contiguous strings have different string patterns and repeating strings, and the elements that make up the strings, are geometrically symmetric to form a repeating central pattern. In a preferred embodiment of the invention, the repeating central pattern consists of two different repeating strings. The central zone 1211 also includes the structural feature 1220 having the denser circular hinge regions 1218. The structural feature 1220 interrupts the repeating pattern in the central zone 1211, such that the repeating pattern of struts and hinges reside before and after the structural feature 1220.

FIG. 23 illustrates the strut strings that are part of the repeating pattern forming the central zone 1211 of the stent 1200 according to one embodiment of the present invention. The central zone 1211 generally has a pattern that includes a connector 1212 or hinge region 1218 attached at every fourth bend or undulation created by pairs of longitudinally adjacent struts 1213 connected by a hinge 1214 as the undulating pattern winds through the helical central zone 1211. That is to say a connector hinge 1214b is followed by three free hinges in the pattern. However, the structural feature 1220, shaded for clarity in FIGS. 22 and 23, had a hinge region at every other undulation and the helical pattern winds through the central zone 1211. The repeating pattern of a connector hinge 1214b followed by three free hinges 1214a continues after the structural feature 1120 until the repeating pattern meets the distal transition zone 1210. The uninterrupted repeating pattern that forms the central zone 1211 is best illustrated by following the pattern starting at the distal end of the central zone 1211. The distal end of the central zone 1211 starts with a connector strut string. The illustrated connector strut string includes a connector hinge 1214b at its proximal and distal ends, and an arrangement of three long (three depot) struts 1213 connected by free hinges 1214a. The free strut string, which follows the connector strut string when winding in a proximal direction, is attached on its distal end to the proximal end of the connector strut string. The illustrated free strut string includes a series of three long (three depot) struts 1213 interconnected by a free hinge 1214a. The three, three depot struts 1213 are connected on each end to a short two depot strut 1213 by free hinges 1214a.

The embodiment illustrated in FIGS. 22 and 23 show the connectors 1212 in the structural feature 1220 all being oriented in the same direction relative to the longitudinal axis. That is, when moving in a distal to proximal direction, all the connectors 1212 connect from the lower end portion of a strut 1213 to the upper portion of the longitudinally adjacent strut 1213. An imaginary line drawn through each connector 1212 would form an acute angle with a line parallel to the longitudinal axis.

Figure 25:
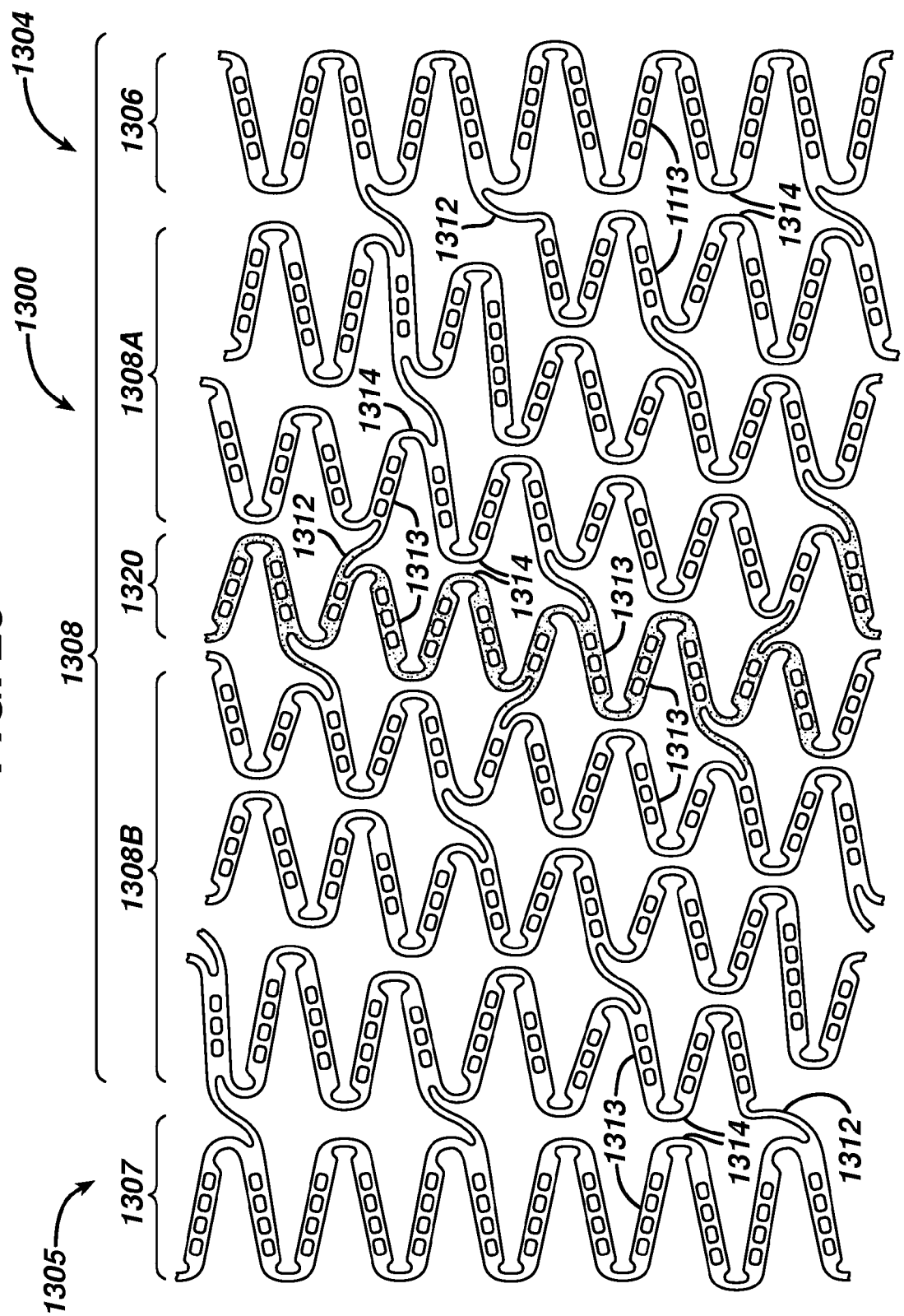
FIG. 25 is a plan view of a flexible stent according to one embodiment of the present invention.
Figure 26:
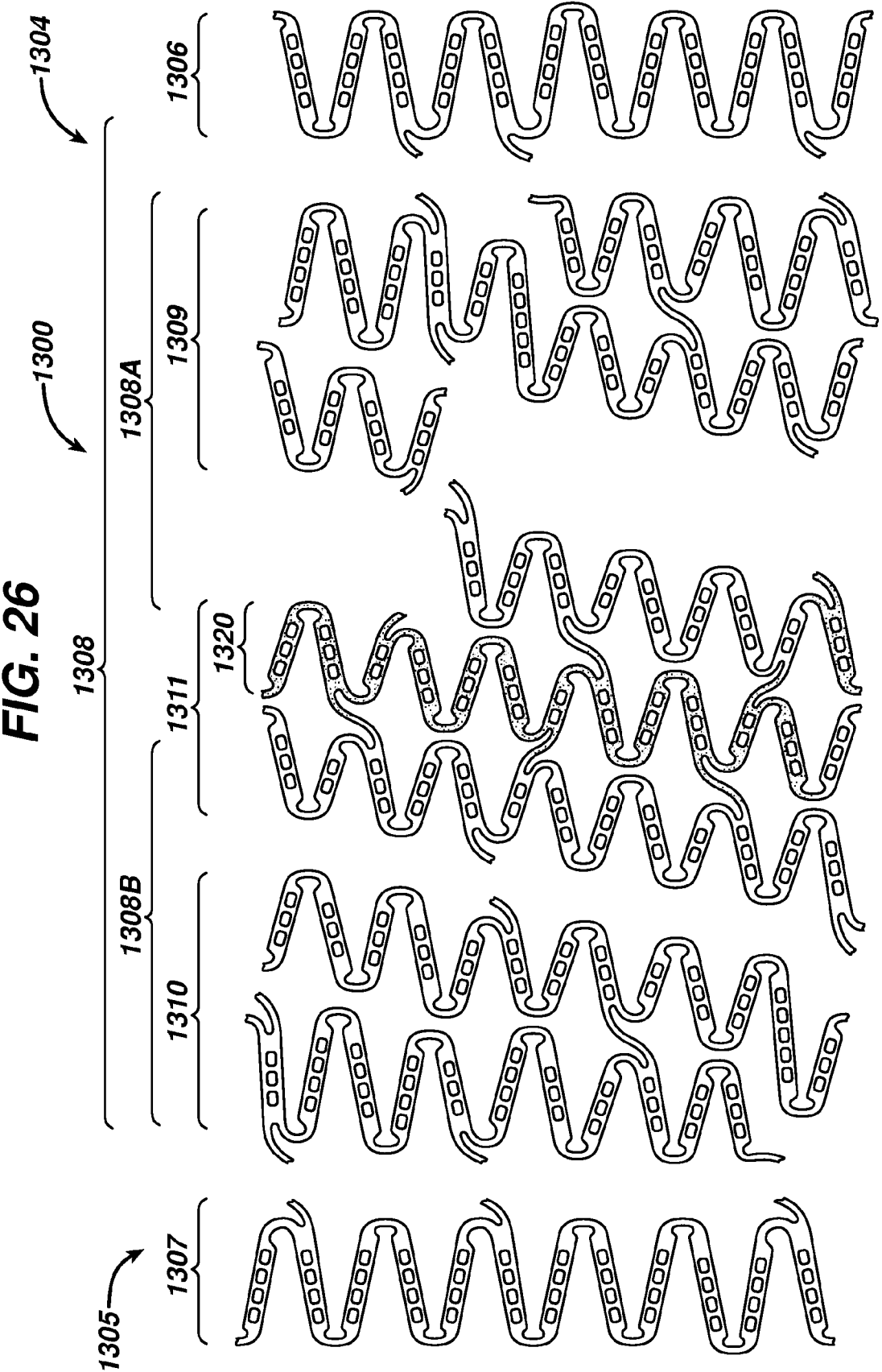
FIG. 26 is an exploded plan view of the flexible stent of FIG. 25.

Another embodiment of the invention contemplates alternating the direction of the connectors 1212 in some pattern. FIGS. 25 and 26 are plan views of a stent 1300 in a partially expanded condition according to one such embodiment of the present invention. Similar to stent 1200 previously disclosed, the stent 1300 architecture generally includes proximal and distal closed ring-like end sections 1306, 1307 along the proximal and distal ends 1304, 1305 respectively, and a substantially helical interior section 1308 there between. The stent 1300 includes a plurality of longitudinally oriented struts 1313 connected by a series of circumferentially oriented ductile hinges 1314. Circumferentially adjacent struts 1313 are connected at opposite ends by the hinges 1314 in a substantially S or Z shaped sinusoidal-like patter to form a band. Flexible connectors 1312 are distributed through the stent 1200 architecture for structural stability under a variety of loading conditions.

In addition, the stent 1300 has a structural feature 1320, shaded for clarity, which includes additional connectors between adjacent helical windings in the central zone 1311. However, unlike the dense band of connectors 1212 forming structural feature 1220 in stent 1200, where all connectors 1212 are oriented in the same direction, the band 1320 of connectors 1312 in stent 1300 have an alternating orientation. That is circumferentially adjacent connectors 1312 alternate between forming an acute angle with the longitudinal axis to obtuse angle with the longitudinal axis. Having connectors 1312 with opposite orientations provides addition shear strengthening when needed.

Figure 27:
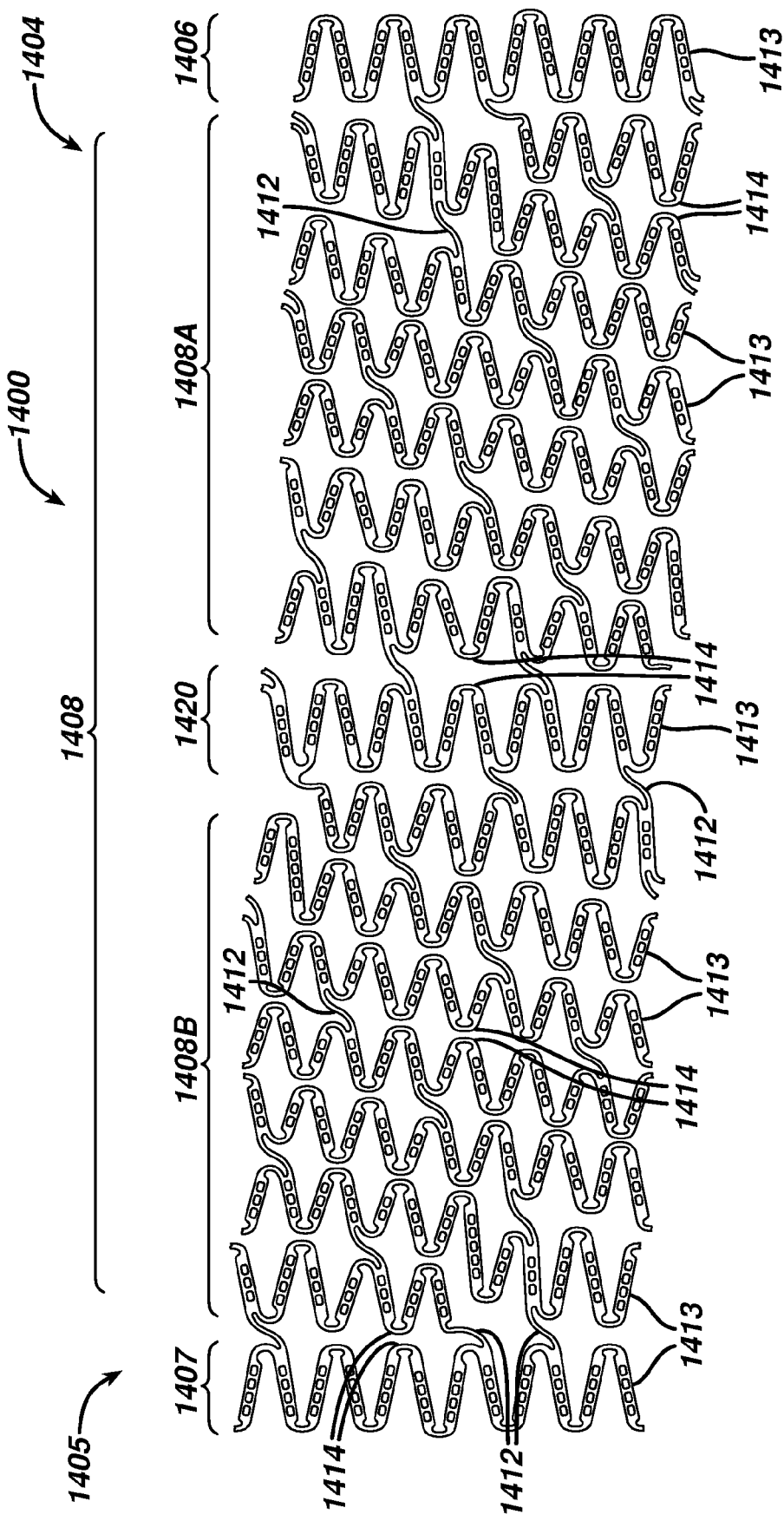
FIG. 27 is a plan view of a flexible stent according to one embodiment of the present invention.
Figure 28:
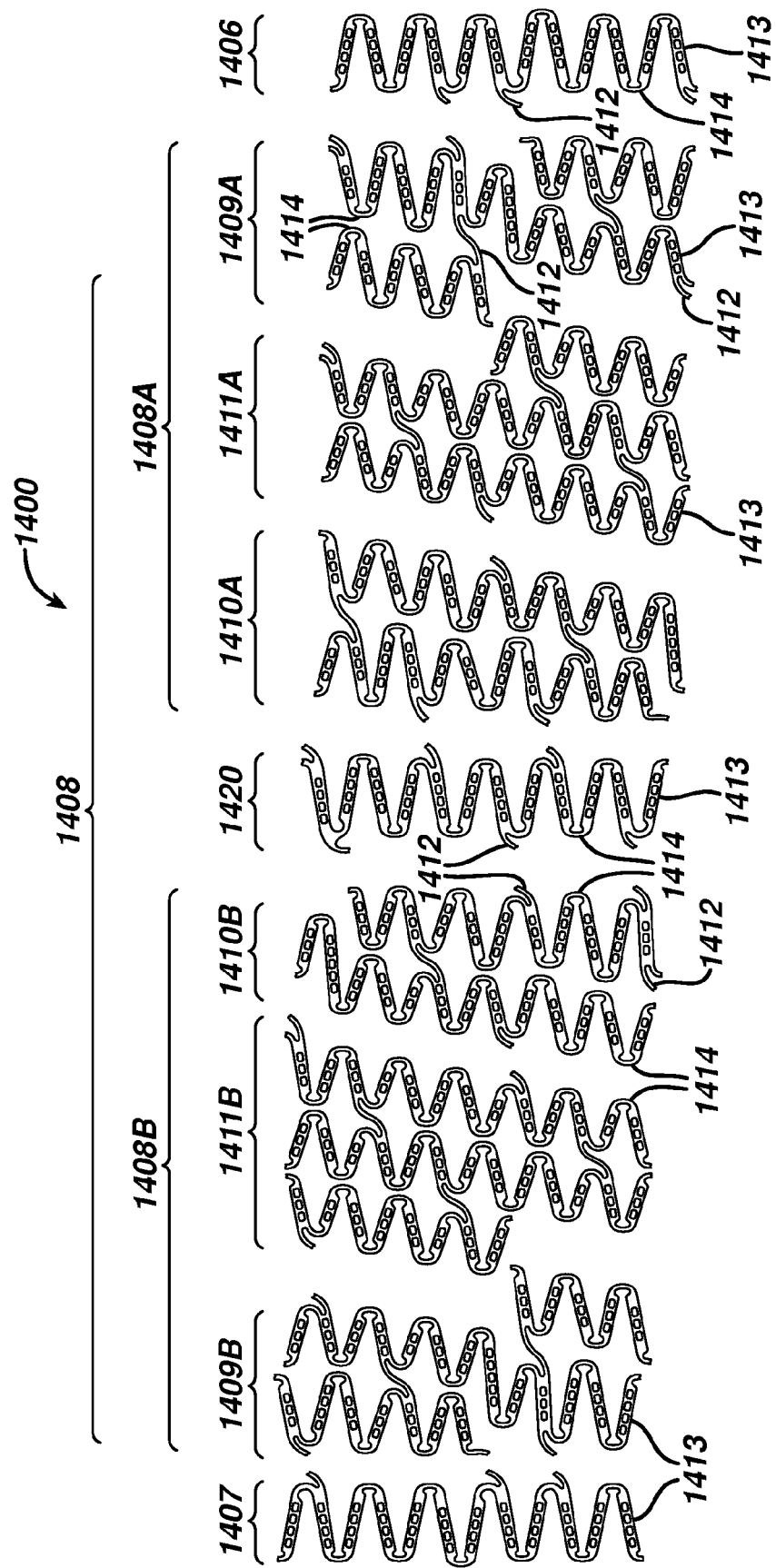
FIG. 28 is an exploded plan view of the flexible stent of FIG. 27.

Another inventive embodiment of a structural feature that interrupts the repeating pattern in the central zone includes a structural feature in the form of a ring-like central section, similar to the ring-like end sections previously described. FIGS. 27 and 28 are plan views of stent 1400 in a partially expanded condition according to one embodiment of the present invention that includes such feature.

The stent 1400 architecture generally includes proximal and distal ring-like end sections 1406, 1407 along the proximal and distal ends 1404, 1405, respectively, and a ring-like central section 1420 located there between. The ring-like sections 1406, 1407 and 1420 are closed hoop structures in axial alignment and define the longitudinal axis. While the illustrated embodiment shows one ring-like structure at each location, the number and relative spacing between the ring-like sections should not be construed a limited factor in the present stent design.

The stent 1400 further includes at least two helical sections between the ring-like sections. In the illustrated embodiment, a first helical section 1408A is located between the proximal ring like end section 1406 and the central ring-like section 1420. A second helical section 1408B is located between the distal ring-like end section 1407 and the central ring-like section 1420. The helical interior sections 1408A, 1408B may each further include a central zone and proximal and distal transition zones.

FIG. 28 is an exploded plan view of stent 1400 illustrating the central and transition sections in each helical section. Particularly, helical interior section 1408A includes a central zone 1411A and proximal and distal transition zones 1409A, 1410A respectively. Similarly, the helical interior section 1418B includes a central zone 1411B and proximal and distal transition zones 1409B, 1410B respectively. The transition zones 1409A,B transitions the helical pattern between the central zones 1411A,B, respectively, and the proximal and distal ring-like end sections 1406, 1407 respectively. The transition zone 1410A,B transitions the helical pattern between the central zone 1411A,B, respectively, and the central ring-like section 1420.

The stent 1400 includes a plurality of longitudinally oriented struts 1413 connected by a series of circumferentially oriented ductile hinges 1414. Circumferentially adjacent struts 1413 are connected at opposite ends by the hinges 1414 in a substantially S or Z shaped sinusoidal-like pattern to form a band. The band forming the ring-like end sections 1406, 1407 and structural feature 1420 are closed rings. The bands forming the central helical sections 1408A,B are wound about the longitudinal axis in a spiral or helical fashion. Flexible connectors 1412 are distributed throughout the stent 1400 architecture for structural stability under a variety of loading conditions. The stent design illustrated in FIGS. 27 and 28 have a flexible connector geometry, however a wide variety of connector geometries are contemplated. See generally FIGS. 6B through 6H.

The central zones 1411A,B may include strings (collections of elements) formed from groups of contiguous strut members 1413 and hinge members 1414 organized to form a string pattern. In one embodiment of the invention, contiguous strings have different string patterns and repeating strings, and the elements that make up the strings, are geometrically symmetric to form a repeating central pattern. In a preferred embodiment of the invention, the repeating central pattern consists of two different repeating strings.

FIG. 28 illustrates the strut strings that are part of the repeating pattern forming the central zones 1411A, 1411B of the stent 1400 according to one embodiment of the present invention. The uninterrupted repeating pattern that forms the central zone 1411 is best illustrated by following the pattern starting at the distal end of the central zone 1411B. The distal end of the central zone 1411B starts with a connector strut string. The illustrated connector strut string includes a connector hinge 1414b at its proximal and distal ends, and an arrangement of three long (three depot) struts 1413 connected by free hinges 1414a. The free strut string, which follows the connector strut string when winding in a proximal direction, is attached on its distal end to the proximal end of the connector strut string. The illustrated free strut string includes a series of three long (three depot) struts 1413 interconnected by a free hinge 1414a. The three, three depot struts 1413 are connected on each end to a short two depot strut 1413 by free hinges 1414a. A similar pattern is found in central zone 1411A. The pattern of strut strings repeats throughout the central zones 1411A, 1411B.

The closed ring forming structural feature 1420 provides a more rigid central area, which allows the stent to be more securely crimped to the expansion balloon. This will improve stent deployment. The design will also reduce the risk of forelengthening during deployment, which will reduce unintended strain to the stent, create greater fracture resistance, and general aid in stent placement by maintaining the stent intended length.

Stent 1400 generally illustrates a stent architecture having a helical section 1408 wound in a distal counter-clockwise direction. That is to say when looking in a distal direction from the proximal end, the helical band is wrapped counter-clockwise around the longitudinal axis in a substantially helical manner from the proximal end 1404 of the stent towards the distal end 1405 of the stent. Another inventive stent design may have one or more helical sections wound in both a distal counter-clockwise and a distal clockwise direction.

Figure 29:
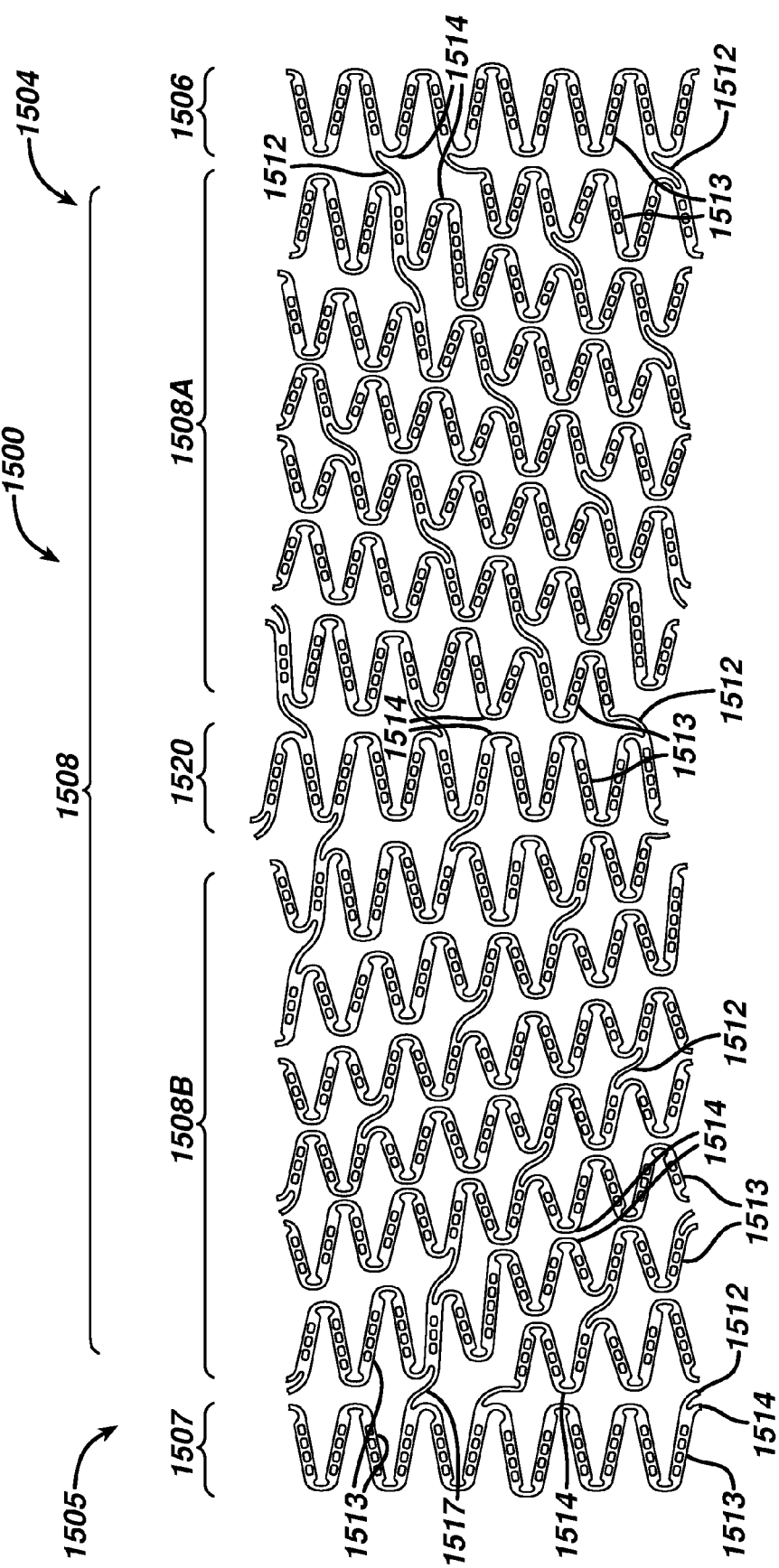
FIG. 29 is a plan view of a flexible stent according to one embodiment of the present invention.
Figure 30:
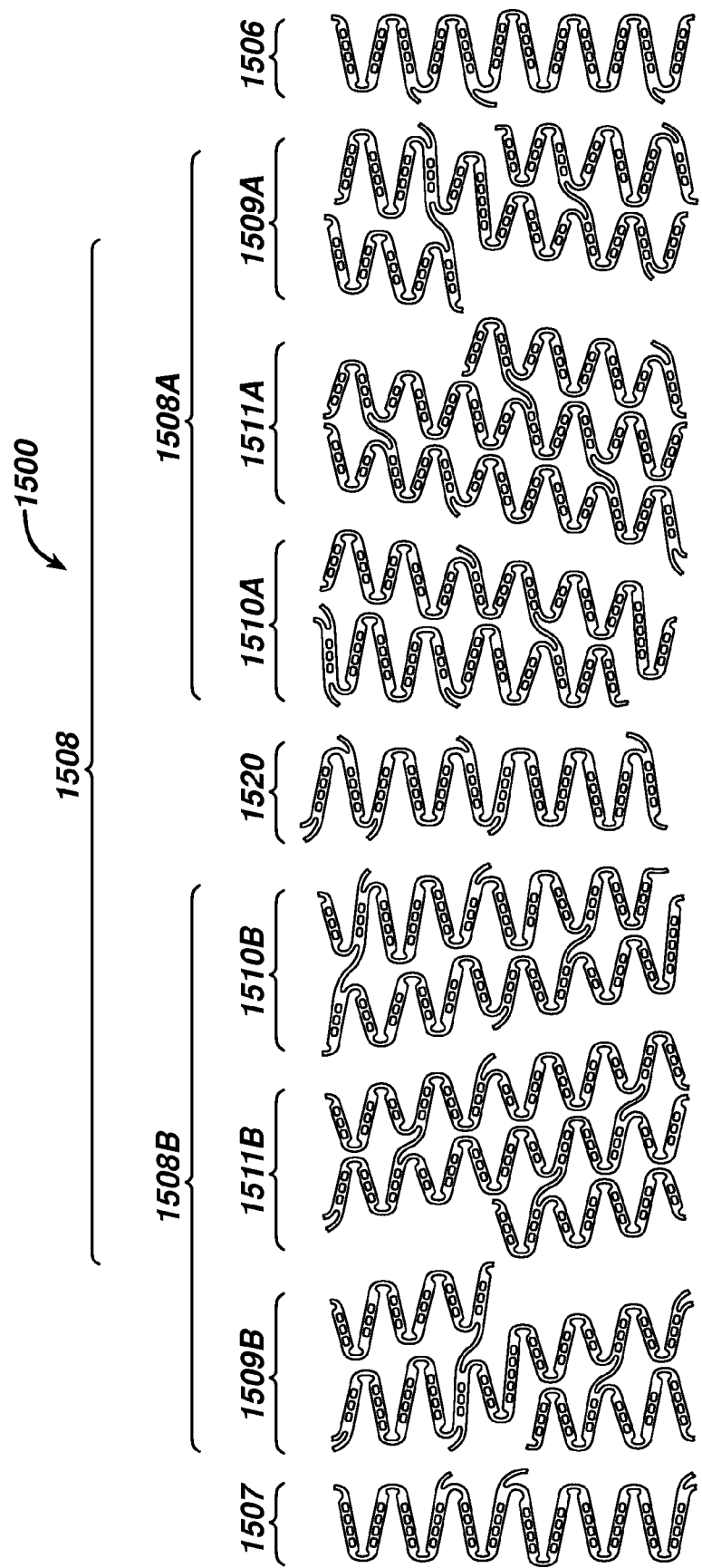
FIG. 30 is an exploded plan view of the flexible stent of FIG. 29.

FIGS. 29 and 30 are plan views of stent 1500 in a partially expanded condition according to one embodiment of the present invention that includes such feature.

The stent 1500 architecture generally includes proximal and distal ring-like end sections 1506, 1507 along the proximal and distal ends 1504, 1505, respectively, and a ring-like central section 1520 located there between. The ring-like sections 1506, 1507 and 1520 are closed hoop structures in axial alignment and define the longitudinal axis. While the illustrated embodiment shows one ring-like structure at each location, the number and relative spacing between the ring-like sections should not be construed a limited factor in the present stent design.

The stent 1500 further includes at least two helical sections between the ring-like sections. In the illustrated embodiment, a first helical section 1508A is located between the proximal ring like end section 1506 and the central ring-like section 1520. A second helical section 1508B is located between the distal ring-like end section 1507 and the central ring-like section 1520. As can be seen in FIGS. 29 and 30, the helical sections 1508A and 1508B are wound in opposite directions.

Particularly, helical section 1508A is wound in a distal counter-clockwise direction. As defined above, a distal counter-clockwise direction means when looking in a distal direction from the proximal end, the helical band is wrapped counter-clockwise around the longitudinal axis in a substantially helical manner from the proximal end 1504 of the stent towards the distal end 1505 of the stent. Conversely, helical section 1508B is wound in a distal clockwise direction. That is to say, when looking in a distal direction from the proximal end, the helical band is wrapped clockwise around the longitudinal axis in a substantially helical manner from the proximal end 1504 of the stent towards the distal end 1505 of the stent.

The helical interior sections 1508A, 1508B may each further include a central zone and proximal and distal transition zones. FIG. 30 is an exploded plan view of stent 1500 illustrating the central and transition sections in each helical section. Particularly, helical interior section 1508A includes a central zone 1511A and proximal and distal transition zones 1509A, 1510A respectively. Similarly, the helical interior section 1508B includes a central zone 1511B and proximal and distal transition zones 1509B, 1510B respectively. The transition zones 1509A,B transitions the helical pattern between the central zones 1511A,B, respectively, and the proximal and distal ring-like end sections 1506, 1507 respectively. The transition zone 1510A,B transitions the helical pattern between the central zone 1511A,B, respectively, and the central ring-like section 1520.

The stent 1500 includes a plurality of longitudinally oriented struts 1513 connected by a series of circumferentially oriented ductile hinges 1514. Circumferentially adjacent struts 1513 are connected at opposite ends by the hinges 1514 in a substantially S or Z shaped sinusoidal-like pattern to form a band. The band forming the ring-like end sections 1506, 1507 and structural feature 1520 are closed rings. The bands forming the central helical sections 1508A,B are wound about the longitudinal axis in a spiral or helical fashion. Flexible connectors 1512 are distributed throughout the stent 1500 architecture for structural stability under a variety of loading conditions. The stent design illustrated in FIGS. 29 and 30 have a flexible connector geometry, however a wide variety of connector geometries are contemplated. See generally FIGS. 6B through 6H.

The central zones 1511A,B may include strings (collections of elements) formed from groups of contiguous strut members 1513 and hinge members 1514 organized to form a string pattern. In one embodiment of the invention, contiguous strings have different string patterns and repeating strings, and the elements that make up the strings, are geometrically symmetric to form a repeating central pattern. In a preferred embodiment of the invention, the repeating central pattern consists of two different repeating strings.

FIG. 30 illustrates the strut strings that are part of the repeating pattern forming the central zones 1511A, 1511B of the stent 1500 according to one embodiment of the present invention. The uninterrupted repeating pattern that forms the central zone 1511 is best illustrated by following the pattern starting at the distal end of the central zone 1511B. The distal end of the central zone 1511B starts with a connector strut string. The illustrated connector strut string includes a connector hinge 1514b at its proximal and distal ends, and an arrangement of three long (three depot) struts 1513 connected by free hinges 1514a. The free strut string, which follows the connector strut string when winding in a proximal direction, is attached on its distal end to the proximal end of the connector strut string. The illustrated free strut string includes a series of three long (three depot) struts 1513 interconnected by a free hinge 1514a. The three, three depot struts 1513 are connected on each end to a short two depot strut 1513 by free hinges 1514a. A similar pattern is found in central zone 1511A. The pattern of strut strings repeats throughout the central zones 1511A, 1511B.

Figure 31:
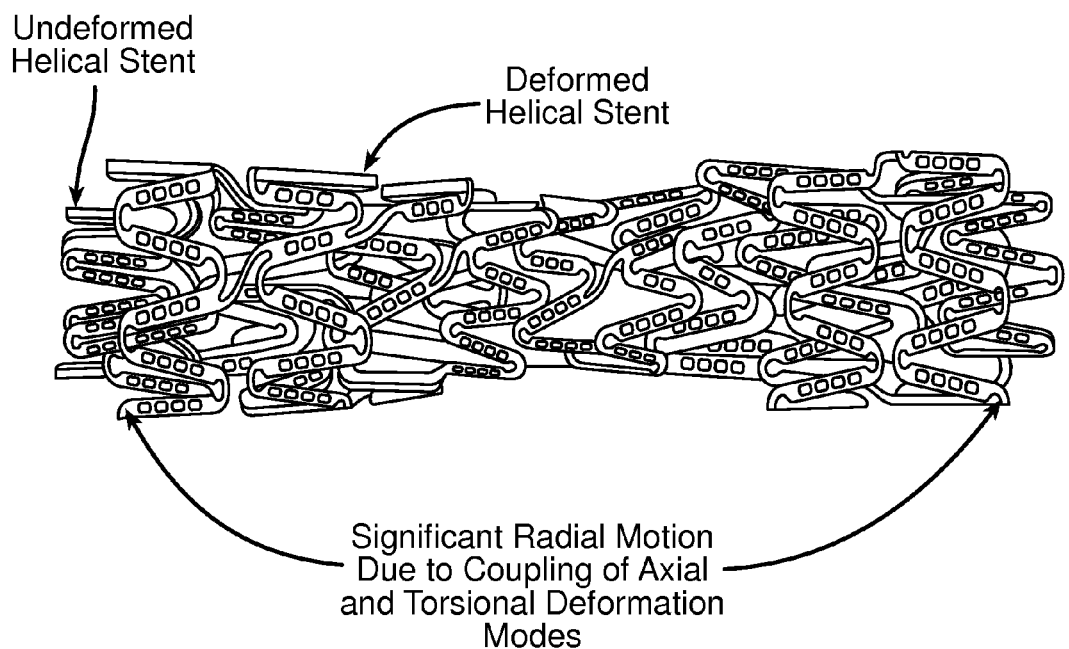
FIG. 31 is a perspective view illustrating a helical stent in the un-deformed and deformed configuration, the latter being overlayed over the former.

This opposing helix design illustrated in the present invention improves stent retention at the ends, as well as at the center of the stent, by dampening axial and torsional deformation modes intrinsic in helical stent designs when subject to compressive load. Such axial compression of the stent is typically encountered when crossing the stent into a tight lesion, or pulling the stent back into the guide catheter. FIG. 31 is an overlay perspective view illustrating a helical stent in the un-deformed and deformed configuration, the latter being overlayed over the former. This superimposition illustrates the coupling of the axial and torsional deformation modes that are experienced by a helical section of the present invention.

As can be seen in FIG. 31, torsional deformation resulting from axial compression tends to deform the stent radially outward, thus adversely impacting stent retention. The two opposing helixes tend to twist in opposite directions, nullifying the unwanted torsional deformation. Reducing or eliminating coupling between axial and torsional deformation modes suppress unwanted torsional deformation and improves stent retention. The two opposing helices tend to twist in opposite directions, thus nullifying the unwanted torsional deformation.

In addition, the closed ring forming structural feature 1520 provides a more rigid central area, which allows the stent to be more securely crimped to the expansion balloon. This will improve stent deployment. The design will also reduce the risk of forelengthening during deployment, which will reduce unintended strain to the stent, create greater fracture resistance, and general aid in stent placement by maintaining the stent intended length.

The stent 1500 depicted in FIGS. 29 and 30 shows struts 1513 in the central feature 1520 with depots 1517 that are capable of holding drug or agent. An alternate design would eliminate the depots 1517. This modification allows for thinner struts 1513, and as a result a greater number of struts 1513 can be used in the central feature 1520. The more struts 1513 can be utilized around the circumference of the center ring-like central feature 1520, the more surface area is available to secure the stent on the balloon catheter. FIG. 32 is a plan view of a modified stent 1500 in a partially expanded configuration according to such alternate embodiment. As can be seen, the ring-like center ring 1520 can accommodate 16 sruts 1513 without depots around the circumference, while the ring-like end sections 1506, 1507 can only accommodate 12 struts 1513 with depots.

What is claimed is:

1. A tubular flexible stent having proximal and distal end portions and a cylindrical shape, with luminal and abluminal surfaces and a thickness there between, the cylindrical shape defining a longitudinal axis, the tubular flexible stent comprising: a proximal helical section, a distal helical section and an intermediate ring section there between, each of the proximal and distal helical sections having of a plurality of longitudinally oriented strut members and a plurality of circumferentially oriented hinge members connecting circumferentially adjacent strut members to form a band, the band being wrapped about the longitudinal axis in a substantially helical manner to form a plurality of helical windings, wherein the distal helical section is wound about the longitudinal axis in the opposite direction from the proximal helical section, wherein no helical windings are proximal of the proximal helical section and no helical windings are distal of the distal helical section, wherein the intermediate ring section comprised of a plurality of longitudinally oriented strut members and a plurality of circumferentially oriented hinge members connecting circumferentially adjacent strut members to form an endless ring, the intermediate ring section being attached to the distal end of the proximal helical section by at least one ring connector member and attached to the proximal end of the distal helical section by at least one ring connector member and wherein each strut member has a substantially rectangular shape with opposing longitudinally oriented long sides and opposing circumferentially oriented short sides, each hinge member being connected to the circumferentially adjacent strut member along the short side of the strut member.

2. The stent of claim 1 wherein helical connector members extend between longitudinally adjacent helical windings of the band.

3. The flexible stent of claim 1 wherein the proximal and distal helical sections each comprise strings formed from groups of contiguous strut members and hinge members organized to form a geometrically symmetric string pattern, and wherein contiguous strings along the band have different string patterns.

4. The stent of claim 1 wherein at least one helical connector member extends between longitudinally adjacent helical windings of the band, the helical connector member being attached to the short sides of longitudinally adjacent strut members, the helical connector member not being attached to longitudinally adjacent hinge members.

5. The flexible stent of claim 1 wherein the hinge and strut members forming the band are arranged in a substantially S or Z shaped sinusoidal-like pattern.

6. The flexible stent of claim 1 wherein the width of each strut member is greater than the width of each hinge member attached to said strut member.

7. The flexible stent of claim 1 wherein the width of at least one strut member tapers along its longitudinal length.

8. The flexible stent of claim 7 wherein the strut member width is greatest at one of the short sides and smallest at the opposing short side.

9. The flexible stent of claim 7 wherein the strut member width is smallest at a point along the strut member length that is between the opposing short sides.

10. The flexible stent of claim 1 wherein at least one of the strut members has at least one depot for loading at least one agent therein.

11. The flexible stent of claim 10 wherein the at least one depot comprises a plurality of depots.

12. The flexible stent of claim 11 wherein the plurality of depots are distributed nearly uniformly throughout the flexible stent.

13. The flexible stent of claim 11 wherein at least two depots of the plurality of depots contain at least one different agent.

14. The flexible stent of claim 11 wherein at least two depots of the plurality of depots contain different concentrations of the same agent.

15. The flexible stent of claim 10 wherein the at least one depot extends through the strut member so as to define a through opening.

16. The flexible stent of claim 15 wherein the at least one depot extends through the strut member from the luminal to the abluminal surface.

17. The flexible stent of claim 10 wherein the at least one depot has a depth less than the thickness of said at least one strut member so as to define a recess.

18. The flexible stent of claim 10 wherein the agent has an abluminal exposed agent surface area equal to the total cross-sectional area of the depot openings in the abluminal surface of the flexible stent, and the flexible stent has an abluminal bare surface area excluding the cross-sectional area of the depot openings in the abluminal surface, the abluminal exposed agent surface area and the abluminal bare surface area equaling the flexible stent total abluminal surface area, wherein the abluminal bare surface area is between 50 percent and 90 percent of the flexible stent total abluminal surface area.

19. The flexible stent of claim 18 wherein the abluminal bare surface area is approximately 75 percent of the flexible stent total abluminal surface area.

20. The flexible stent of claim 10 wherein the agent has an exposed agent surface area equal to the total cross-sectional area of the depot openings in the surfaces of the flexible stent, and the flexible stent has a bare surface area excluding the cross-sectional area of the depot openings in the surfaces, the exposed agent surface area and the bare surface area equaling the flexible stent total surface area, wherein the bare surface area is between 40 percent and 90 percent of the flexible stent total surface area.

21. The flexible stent of claim 10 wherein the at least one depot comprises at least two agents with a barrier layer between the agents.

22. The flexible stent of claim 21 wherein the at least one barrier layer is oriented substantially parallel to the luminal surface.

23. The flexible stent of claim 1 wherein each of the proximal and distal helical sections comprise a proximal transition zone, a distal transition zone, and a central zone there between, each having a pitch and an incident angle, wherein the pitch and incident angle of the proximal and distal transition zones are different than the central zone.

24. The flexible stent of claim 23 wherein the central zone has a constant pitch and incident angle.

25. The flexible stent of claim 23 wherein the proximal transition zone and distal transition zone each have a variable pitch and incident angle.

26. The flexible stent of claim 23 wherein the central zone comprises strings formed from groups of contiguous strut members and hinge members organized to form a string pattern, wherein contiguous strings along the band have different string patterns.

27. The flexible stent of claim 26 wherein the central section comprises repeating strings that are symmetric to form a repeating central pattern.

28. The flexible stent of claim 27 where the repeating central pattern consists of two different repeating strings.

29. The flexible stent of claim 1 further comprising: a proximal end ring comprised of a plurality of longitudinally oriented strut members and a plurality of circumferentially oriented hinge members connecting circumferentially adjacent strut members to form an endless ring, the proximal end ring being attached to the proximal end of the helical section by at least one ring connector member; and a distal end ring comprised of a plurality of longitudinally oriented strut members and a plurality of circumferentially oriented hinge members connecting circumferentially adjacent strut members to form an endless ring, the distal end ring being attached to the distal end of the helical section by at least one ring connector member.

* * * * *